(12) United States Patent
Bao et al.

(10) Patent No.: US 9,404,883 B2
(45) Date of Patent: Aug. 2, 2016

(54) ELECTRONIC MEASUREMENTS OF MONOLAYERS FOLLOWING HOMOGENEOUS REACTIONS OF THEIR COMPONENTS

(71) Applicant: OHMX CORPORATION, Evanston, IL (US)

(72) Inventors: Yijia Paul Bao, Vernon Hill, IL (US); Adam G. Gaustad, Chicago, IL (US)

(73) Assignee: OHMX Corporation, Evanston, IL (US)

( * ) Notice: Subject to any disclaimer, the term of this patent is extended or adjusted under 35 U.S.C. 154(b) by 544 days.

(21) Appl. No.: 13/952,215

(22) Filed: Jul. 26, 2013

(65) Prior Publication Data

US 2014/0027309 A1 Jan. 30, 2014

Related U.S. Application Data

(60) Provisional application No. 61/676,641, filed on Jul. 27, 2012, provisional application No. 61/677,593, filed on Jul. 31, 2012.

(51) Int. Cl.
*G01N 27/327* (2006.01)
*C12Q 1/28* (2006.01)
*G01N 33/543* (2006.01)

(52) U.S. Cl.
CPC .............. *G01N 27/3277* (2013.01); *C12Q 1/28* (2013.01); *G01N 27/3276* (2013.01); *G01N 33/5438* (2013.01); *G01N 2610/00* (2013.01)

(58) Field of Classification Search
CPC ............ G01N 27/327; G01N 27/3271; G01N 27/3272; G01N 27/3276; G01N 33/53; G01N 33/5302; G01N 33/5306
See application file for complete search history.

(56) References Cited

U.S. PATENT DOCUMENTS

| | | | |
|---|---|---|---|
| 4,247,533 A | 1/1981 | Cerami et al. |
| 4,304,853 A | 12/1981 | Jozefonvicz et al. |
| 4,727,036 A | 2/1988 | Knowles et al. |
| 4,806,468 A | 2/1989 | Wagner et al. |
| 5,206,144 A | 4/1993 | Zeuthen et al. |
| 5,270,163 A | 12/1993 | Gold et al. |
| 5,407,759 A | 4/1995 | Ohsuga |
| 5,475,096 A | 12/1995 | Gold et al. |
| 5,567,588 A | 10/1996 | Gold et al. |

(Continued)

FOREIGN PATENT DOCUMENTS

| | | |
|---|---|---|
| EP | 02075339 | 7/2009 |
| WO | 90/01559 | 2/1990 |

(Continued)

OTHER PUBLICATIONS

Bickert, P., et al., "Pentafulvenes: Versatile Synthons in Metallocene Chemistry," Organometallics, May 1984, vol. 3 (5), pp. 654-657.

(Continued)

*Primary Examiner* — Alexander Noguerola
(74) *Attorney, Agent, or Firm* — Wolf, Greenfield & Sacks, P.C.

(57) ABSTRACT

The disclosure relates to novel methods for performing a solution based assay reaction with an electroactive active moiety (EAM) that subsequently forms a self-assembled monolayer (SAM) utilizing the advantages of faster solution reaction kinetics, SAM protected electrode and surface based electrochemistry for electronic measurement.

18 Claims, 7 Drawing Sheets

(56) References Cited

U.S. PATENT DOCUMENTS

| | | |
|---|---|---|
| 5,595,877 A | 1/1997 | Gold et al. |
| 5,620,850 A | 4/1997 | Bamdad et al. |
| 5,637,459 A | 6/1997 | Burke et al. |
| 5,654,159 A | 8/1997 | Allard et al. |
| 5,683,867 A | 11/1997 | Biesecker et al. |
| 5,705,337 A | 1/1998 | Gold et al. |
| 5,834,224 A | 11/1998 | Ruger et al. |
| 6,013,170 A | 1/2000 | Meade |
| 6,013,459 A | 1/2000 | Meade |
| 6,162,645 A | 12/2000 | Lee et al. |
| 6,248,229 B1 | 6/2001 | Meade |
| 6,348,319 B1 | 2/2002 | Braach-Maksvytis et al. |
| 6,432,723 B1 | 8/2002 | Plaxco et al. |
| 6,495,336 B1 | 12/2002 | Ludin et al. |
| 6,600,026 B1 | 7/2003 | Yu |
| 6,740,518 B1 | 5/2004 | Duong et al. |
| 6,770,190 B1 | 8/2004 | Milanovski et al. |
| 6,927,039 B2 | 8/2005 | Gilardi et al. |
| 6,942,771 B1 | 9/2005 | Kayyem |
| 6,991,926 B2 | 1/2006 | Schmid et al. |
| 7,018,523 B2 | 3/2006 | Meade |
| 7,160,678 B1 | 1/2007 | Kayyem et al. |
| 7,223,837 B2 | 5/2007 | De Groot et al. |
| 7,267,939 B2 | 9/2007 | Meade |
| 7,312,087 B2 | 12/2007 | Duong et al. |
| 7,393,645 B2 | 7/2008 | Kayyem et al. |
| 7,514,228 B2 | 4/2009 | Meade |
| 7,560,237 B2 | 7/2009 | O'Connor et al. |
| 7,566,534 B2 | 7/2009 | Meade |
| 7,579,145 B2 | 8/2009 | Meade |
| 7,582,419 B2 | 9/2009 | Meade |
| 7,595,153 B2 | 9/2009 | Meade |
| 7,601,507 B2 | 10/2009 | O'Connor et al. |
| 7,705,045 B2 | 4/2010 | De Groot et al. |
| 7,713,711 B2 | 5/2010 | O'Connor et al. |
| 7,732,140 B2 | 6/2010 | Vandenbark et al. |
| 7,759,073 B2 | 7/2010 | O'Connor et al. |
| 7,759,114 B2 | 7/2010 | Martin et al. |
| 7,803,572 B2 | 9/2010 | Braven et al. |
| 7,807,835 B2 | 10/2010 | Xie et al. |
| 8,114,661 B2 | 2/2012 | O'Connor et al. |
| 8,530,170 B2 | 9/2013 | Bertin |
| 8,734,631 B2 | 5/2014 | Ahrens et al. |
| 8,802,390 B2 | 8/2014 | Bertin et al. |
| 8,951,400 B2 | 2/2015 | Ahrens et al. |
| 9,194,836 B2 | 11/2015 | Bertin |
| 2002/0058329 A1 | 5/2002 | Singh et al. |
| 2002/0086443 A1 | 7/2002 | Bamdad |
| 2002/0121314 A1 | 9/2002 | Tao et al. |
| 2002/0142411 A1 | 10/2002 | Hainfeld |
| 2003/0073243 A1 | 4/2003 | Law et al. |
| 2003/0119208 A1 | 6/2003 | Yoon et al. |
| 2004/0018611 A1 | 1/2004 | Ward et al. |
| 2004/0023258 A1 | 2/2004 | Patolsky et al. |
| 2005/0123948 A1 | 6/2005 | Claycomb et al. |
| 2005/0148101 A1 | 7/2005 | Bamdad et al. |
| 2005/0189240 A1 | 9/2005 | Lin et al. |
| 2006/0003382 A1 | 1/2006 | Eckermann et al. |
| 2006/0134713 A1 | 6/2006 | Rylatt et al. |
| 2007/0111224 A1 | 5/2007 | Jung et al. |
| 2008/0081329 A1 | 4/2008 | Elliott et al. |
| 2008/0164154 A1 | 7/2008 | Purvis |
| 2008/0248592 A1 | 10/2008 | Bamdad et al. |
| 2009/0041791 A1 | 2/2009 | Feng |
| 2009/0061451 A1 | 3/2009 | Achim et al. |
| 2009/0099434 A1 | 4/2009 | Liu et al. |
| 2009/0107852 A1 | 4/2009 | Labgold et al. |
| 2009/0253149 A1 | 10/2009 | Ahrens et al. |
| 2010/0003710 A1 | 1/2010 | Bertin et al. |
| 2010/0025264 A1 | 2/2010 | Yuan et al. |
| 2010/0145036 A1 | 6/2010 | Sufi et al. |
| 2010/0204554 A1 | 8/2010 | Say et al. |
| 2010/0291591 A1 | 11/2010 | Wick et al. |
| 2011/0033869 A1 | 2/2011 | Bertin |
| 2011/0189705 A1 | 8/2011 | Gao et al. |
| 2012/0012472 A1 | 1/2012 | Ahrens et al. |
| 2012/0034638 A1 | 2/2012 | Ahrens et al. |
| 2012/0156709 A1 | 6/2012 | Bertin et al. |
| 2012/0181186 A1 | 7/2012 | Bertin et al. |
| 2012/0199499 A1 | 8/2012 | O'Connor et al. |
| 2013/0098777 A1 | 4/2013 | Gaustad |
| 2013/0112572 A1 | 5/2013 | Bertin et al. |
| 2013/0236909 A1 | 9/2013 | Bertin |
| 2013/0264220 A1 | 10/2013 | Bertin et al. |
| 2014/0027310 A1 | 1/2014 | Gaustad et al. |
| 2014/0134658 A1 | 5/2014 | Ahrens et al. |
| 2014/0311922 A1 | 10/2014 | Ahrens et al. |
| 2014/0322740 A1 | 10/2014 | Ahrens et al. |
| 2014/0342383 A1 | 11/2014 | Bertin et al. |
| 2015/0192538 A1 | 7/2015 | Ahrens et al. |
| 2015/0198552 A9 | 7/2015 | Ahrens et al. |
| 2015/0323484 A1 | 11/2015 | Bao et al. |
| 2016/0041118 A1 | 2/2016 | Bao |

FOREIGN PATENT DOCUMENTS

| | | |
|---|---|---|
| WO | 93/03379 | 2/1993 |
| WO | 98/57159 A1 | 12/1998 |
| WO | 99/57317 A1 | 11/1999 |
| WO | 00/11474 | 3/2000 |
| WO | 03/019171 | 3/2003 |
| WO | 2008/045799 | 4/2008 |
| WO | 2009/052422 | 4/2009 |
| WO | 2010/142037 | 12/2010 |
| WO | 2011/041586 | 4/2011 |
| WO | 2011/146143 A2 | 11/2011 |
| WO | 2011/150186 A1 | 12/2011 |

OTHER PUBLICATIONS

Farrington, E.J., et al., "Synthesis and reactivity of a ferrocene-derived PCP-pincer ligand," Chem. Commun., Jan. 21, 2002, pp. 308-309.

Gardner, J.W., et al., "Application of conducting polymer technology in microsystems," Sensors and Actuators, Oct. 1995, vol. 51(1), pp. 57-66. (Abstract only).

Heinze, K., et al., "Main Chain Ferrocenyl Amides from 1-Aminoferrocene-1'-carboxylic Acid," Eur. J. Inorg. Chem., Jul. 2004, vol. 2004(14), pp. 2974-2988. (Abstract only).

Heinze, K., et al., "Anion-Induced Motion in a Ferrocene Diamide," Eur. J. Inorg. Chem., Jan. 2005, vol. 2005 (1), pp. 66-71. (Abstract only).

Holleman-Wiberg, Inorganic Chemistry, Academic Press 34th Ed., at 1620. (Abstract unavailable).

Hunter, T., "Protein kinases and phosphatases: the yin and yang of protein phosphorylation and signaling," Cell,1995, vol. 80(2), pp. 225-236. (Abstract unavailable).

Karin, M., "Signal transduction and gene control," Curr. Opin. Cell Biol., Jun. 1991, vol. 3(3), pp. 467-473. (Abstract only).

Li, et al., Current Medicinal Chemistry, 2001, vol. 8, pp. 121-133. (Abstract unavailable).

Pichon, et al., "A direct meta-lithiation route to 1,3-disubstituted ferrocenes," Chem. Commun., Feb. 10, 2004, pp. 598-599.

Steurer, et al., "Bromide-Mediated ortho-Deprotonation in the Synthesis of Chiral, Nonracemic Ferrocene Derivatives," Organometallics, Jun. 19, 2007, vol. 26, pp. 3850-3859.

Eur. J. Biochem, 1995, vol. 232, pp. 1-6. (Abstract unavailable).

Eur. J. Biochem, 1996, vol. 237, pp. 1-5. (Abstract unavailable).

Eur. J. Biochem, 1997, vol. 250, pp. 1-6. (Abstract unavailable).

Eur. J. Biochem, 1999, vol. 264, pp. 610-650. (Abstract unavailable).

Abel, et al., Comprehensive Organometallic Chemistry II, A Review of the Literature 1982-1994, vol. 7, chapters 7, 8, 10 & 11, Pergamon Press (abstract unavailable).

Bertin, P.A., et al., "Novel redox active bifunctional crosslinkers from unsymmetrical 1,1'-disubstituted ferrocenes," Tetrahedron Lett., Sep. 23, 2009, vol. 50(38), pp. 5409-5412 (abstract only).

Chen, C., et al., "Chemically Modified Electrodes by Nucleophilic Substitution of Chlorosilylated Platinum Oxide Surfaces," Langmuir, Sep. 1994, vol. 10(9), pp. 3332-3337 (abstract only).

(56) References Cited

OTHER PUBLICATIONS

Connelly, et al., "Chemical Redox Agents for Organometallic Chemistry," Chem. Rev., Jan. 9, 1996, vol. 96, pp. 877-910.
Cotton, et al., Advanced Organic Chemistry, 5th Edition, John Wiley & Sons, 1988, p. 38; and chapter 26 (abstract unavailable).
Deinhammer et al., "Electrochemical oxidation of amine-containing compounds: a route to the surface modification of glassy carbon electrodes," Langmuir, 1994, vol. 10(4), pp. 1306-1313 (abstract only).
Gassman, et al., "(Trifluoromethyl)cyclopentadienide: a powerful electron-withdrawing ligand for transition-metal complexes," J. Am. Chem. Soc., Jul. 1986, vol. 108(14), pp. 4228-4229 (abstract only).
Geiger, et al., Advances in Organometallic Chemistry, vol. 23, pp. 1-93 (abstract unavailable).
Geiger, et al., Advances in Organometallic Chemistry, vol. 24, p. 87 (abstract unavailable).
Gray, et al., "Electron Transfer in Proteins," Annual Rev. Biochem, 1996, vol. 65, p. 537-561.
Lenhard, J.R., et al., J. Electroanal. Chem., 1977, vol. 78, pp. 195-201 (abstract unavailable).
Li, et al., "Nanoscale 1,3,5,7-Tetrasubstituted Adamantanes and p-Substituted Tetraphenyl-methanes for AFM Applications," Org. Lett., Sep. 18, 2002, vol. 4(21), pp. 3631-3634 (abstract only).
Lo, L., et al., "Development of highly selective and sensitive probes for hydrogen peroxide," Chem. Commun., 2003, pp. 2728-2729.
Robbins, et al., "Syntheses and electronic structures of decamethylmetallocenes," J. Am. Chem. Soc., Apr. 1982, vol. 104(7), pp. 1882-1893 (abstract only).
Sagi, et al.,"Amperometric Assay for Aldolase Activity; Antibody-Catalyzed Ferrocenylamine Formation," Anal. Chem., 2006, vol. 78(5), pp. 1459-1461 (abstract only).
Sella, E., et al., "Self-immolative dendritic probe for the direct detection of triacetone triperoxide," Chem. Commun., Oct. 15, 2008, Issue 44, pp. 5701-5703 (abstract only).
Wei, et al., "Diverse Redox-Active Molecules Bearing Identical Thiol-Terminated Tripodal Tethers for Studies of Molecular Information Storage," J. Org. Chem., 2004, vol. 69(5), pp. 1461-1469 (abstract only).
Comprehensive Coordination Chemistry, Ed., Wilkinson et al., Pergammon Press, 1987, Chapters 13.2, pp. (73-98), 21.1, pp. (813-898), and 21.3, pp. 915-957 (abstract unavailable).
Xiang, Yu, et al., "Using personal glucose meters and functional DNA sensors to quantify a variety of analytical targets," Nature Chemistry, Sep. 2011, vol. 3, pp. 697-703.
International Search Report and Written Opinion dated Jan. 7, 2014 for Application No. PCT/US2013/052340.
International Search Report and Written Opinion dated Jan. 31, 2014 for Application No. PCT/US2013/052324.
Anne et al., Optimizing electrode-attached redox-peptide systems for kinetic characterization of protease action on immobilized substrates. Observation of dissimilar behavior of trypsin and thrombin enzymes. Langmuir. Jun. 12, 2012;28(23):8804-13. Epub May 24, 2012.
Garcia et al., Electrochemical DNA base pairs quantification and endonuclease cleavage detection. Biosens Bioelectron. Sep. 15, 2011;27(1):40-5. Epub Jun. 15, 2011.
Sato et al., Reliable ferrocenyloligonucleotide-immobilized electrodes and their application to electrochemical DNase I assay. Anal Chim Acta. Jul. 10, 2009;645(1-2):30-5. Epub May 6, 2009.
Shipovskov et al., Electrochemical sandwich assay for attomole analysis of DNA and RNA from beer spoilage bacteria *Lactobacillus brevis*. Biosens Bioelectron. Aug.-Sep. 2012;37(1):9-106. Epub May 11, 2012.
Adjemian, Jocelyne, et al., "Cleavage-Sensing Redox Peptide Monolayers for the Rapid Measurement of the Proteolytic Activity of Trypsin and a-Thrombin Enzymes," Langmuir, Jan. 27, 2010, vol. 26(12), pp. 10347-10356.
Chin, Curtis D., et al, "Microfluidics-Based Diagnostics of Infectious Diseases in the Developing World," Nature Medicine, 2011, vol. 17, pp. 1015-1019, available online Jul. 31, 2011.
Gaster, Richard S., et al., "nanoLAB: An Ultraportable, Handheld Diagnostic Laboratory for Global Health," Lab on a Chip, Dynamic Article Links, Jan. 24, 2011, pp. 1-7.
Houseman, Benjamin T., et al., "Peptide Chips for the Quantitative Evaluation of Protein Kinase Activity," Nature Biotechnology, Research Article, Mar. 2002, vol. 20, pp. 270-274.
Kerman, Kagan, et al., "Electrochemical Detection of Kinase-Catalyzed Thiophosphorylation Using Gold Nanoparticles," Chem. Commun. 2007, pp. 5019-5021.
Kerman, Kagan, et al., "Peptide Biosensors for the Electrochemical Measurement of Protein Kinase Activity," Anal. Chem., 2008, vol. 80, pp. 9395-9401.
Kerman, Kagan, et al., "Electrochemical Detection of Protein Tyrosine Kinase-Catalysed Phosphorylation Using Gold Nanoparticles," Biosensors and Bioelectronics, 2009, vol. 24, pp. 1484-1489.
Kim, S.D., et al., "Gold-Film Array-Electrode for Electrochemical ELISA," Sensors and Actuators B, 2005, pp. 463-469.
Labib, Mahmoud, et al., "A Bioorganometallic Approach for Rapid Electrochemical Analysis of Human Immunodeficiency Virus Type-1 Reverse Transcriptase in Serum," Elsevier, Article in Press, Electrochimica Acta, available online Mar. 22, 2011, pp. 1-7.
Leinonen, J., et al., "Development of Novel Peptide Ligands Modulating the Enzyme Activity of Prostate-Specific Antigen," Scand. J. Clin. Lab. Invest., 2000, pp. 59-64.
Li, Peng, et al., "Development of an Ultrafast Quantitative Heterogeneous Immunoassay on Prefunctionalized Poly(Dimethylsiloxane), Microfluidic Chips for the Next-Generation Immunosensors," Microfluidics and Nanofluidics, vol. 7, No. 4, Mar. 11, 2009.
Martic, Sanela, et al., "Probing the Role of the Linker in Ferrocene-ATP Conjugates: Monitoring Protein Kinase Catalyzed Phosphorylations Electrochemically," Chemistry—A European Journal, 2011, vol. 17, pp. 6744-6752.
Martic, Sanela, et al., "Use of 5-y-Ferrocenyl Adenosine Triphosphate (Fc-ATP) Bioconjugates Having Poly (ethylene glycol) Spacers in Kinase-Catalyzed Phosphorylations," Bioconjugate Chemistry, 2011, pp. 1-10.
Martic, Sanela, et al., "Enzymatically Modified Peptide Surfaces: Towards General Electrochemical Sensor Platform for Protein Kinase Catalyzed Phosphorylations," Analyst, 2011, vol. 136, pp. 107-112.
Nagy, Geza, et al., "Screen-Printed Amperometric Microcell for Proline Iminopeptidase Enzyme Activity Assay," Biosensors & Bioelectronics, 2000, vol. 15, pp. 265-272.
Song, Haifeng, et al., "Electrochemical Detection of Kinase-Catalyzed Phosphorylation Using Ferrocene-Conjugated ATP," Chem. Commun., 2008, pp. 502-504.
Vukmirovic-Popovic, Snezana, et al., "Presence and Enzymatic Activity of Prostate-Specific Antigen in Archival Prostate Cancer Samples," Oncology Reports, 2008, vol. 20, pp. 897-903.
Zhou, Ya-Min, et al., "An Amperometric Immunosensor Based on an Electrochemically Pretreated Carbon-Paraffin Electrode for Complement III (C3) Assay," Biosensors and Bioelectronics, 2008, vol. 18, pp. 473-481.
Batchelor, Robert, et al., "A Resorufin-Based Fluorescent Assay for Quantifying NADH," Analytical Biochemistry, 2002, vol. 305, pp. 118-119.
Beckett, Dorothy, et al., "A Minimal Peptide Substrate in Biotin Holoenzyme Synthetase-Catalyzed Biotinylation," Protein Science, 1999, vol. 8, pp. 921-929.
Collman, et al., "Role of a Distal Pocket in the Catalytic O2 Reduction by Cytochrome C Oxidase Models Immobilized on Interdigitated Array Electrodes," PNAS, 2009, vol. 106, No. 18, pp. 7320-7323.
Cronan, John E., Jr., "The *E. coli* bio Operon: Transcriptional Repression by an Essential Protein Modification Enzyme," Cell, 1989, vol. 58, pp. 427-429.
Hudson, Richard D.A., "Ferrocene Polymers: Current Architectures, Syntheses and Utility," Journal of Organometallic Chemistry, 2001, pp. 47-69, Abstract only.

(56) References Cited

OTHER PUBLICATIONS

Kamidate, Tamio, et al., "Firefly Bioluminescent Assay of ATP in the Presence of ATP Extractant by Using Liposomes," Anal. Chem., 2006, vol. 78, pp. 337-342.

Llaudet, Enrique, et al., "Microelectrode Biosensor for Real-Time Measurement of ATP in Biological Tissue," Anal. Chem., 2005, vol. 77, pp. 3267-3273.

Murphy, Lindy J., et al., "Measurement in Vitro of Human Plasma Glycerol with a Hydrogen Peroxide Detecting Microdialysis Enzyme Electrode," Anal. Chem., 1994, vol. 66, pp. 4345-4353.

Tabata, Masayoshi, et al., "Use of a Biosensor Consisting of an Immobilized NADH Oxidase Column and a Hydrogen Peroxide Electrode for the Determination of Serum Lactate Dehydrogenase Activity," Analytica Chimica Acta, 1994, vol. 298, pp. 113-119.

Wang, Yonghong, et al., "A Sensitive Ligase-Based ATP Electrochemical Assay Using Molecular Beacon-Like DNA," Biosensors and Bioelectronics, 2010, vol. 25, pp. 2101-2106.

Spinke, J., et al., "Molecular Recognition at self-assembled monolayers: Optimization of surface functionalization," The Journal of Chemical Physics, vol. 99, No. 9, Nov. 1993, pp. 7012-7018.

Spinke, J., et al., "Molecular Recognition at self-assembled monolayers: The construction of multicomponent multilayers," Langmuir, 1993, vol. 9(7), pp. 1821-1825.

U.S. Appl. No. 13/667,713, filed Nov. 2, 2012, Bertin et al.
U.S. Appl. No. 14/934,765, filed Nov. 6, 2015, Bertin et al.
U.S. Appl. No. 14/593,318, filed Jan. 9, 2015, Ahrens et al.
U.S. Appl. No. 14/974,736, filed Dec. 18, 2015, Bertin et al.
U.S. Appl. No. 14/700,062, filed Apr. 29, 2015, Bao et al.
U.S. Appl. No. 14/824,045, filed Aug. 11, 2015, Bao et al.
U.S. Appl. No. 14/863,397, filed Sep. 23, 2015, Georganopoulou.
U.S. Appl. No. 14/975,669, filed Dec. 18, 2015, Gaustad.
U.S. Appl. No. 14/281,865, filed May 19, 2014, Bertin et al.
U.S. Appl. No. 14/254,817, filed Apr. 16, 2014, Ahrens et al.
U.S. Appl. No. 13/793,752, filed Mar. 11, 2013, Bertin.
U.S. Appl. No. 13/667,713, filed Nov. 2, 2012, Bertin.
U.S. Appl. No. 13/068,938, filed May 23, 2011, Ahrens et al.
U.S. Appl. No. 13/798,461, filed Mar. 13, 2013, Ahrens et al.
U.S. Appl. No. 13/187,142, filed Jul. 20, 2011, Ahrens et al.
U.S. Appl. No. 14/033,169, filed Sep. 20, 2013, Ahrens et al.
U.S. Appl. No. 13/952,345, filed Jul. 26, 2013, Gaustad et al.
U.S. Appl. No. 13/354,200, filed Jan. 19, 2012, Bertin et al.
U.S. Appl. No. 13/653,931, filed Oct. 17, 2012, Gaustad et al.
U.S. Appl. No. 13/737,634, filed Jan. 9, 2013, Bertin et al.
PCT/US2013/052340, Jan. 7, 2014, International Search Report and Written Opinion.
PCT/US2013/052324, Jan. 31, 2014, International Search Report and Written Opinion.

ELECTRONIC MEASUREMENTS OF MONOLAYERS FOLLOWING HOMOGENEOUS REACTIONS OF THEIR COMPONENTS

CROSS-REFERENCE TO RELATED APPLICATIONS

This application claims the benefit of priority to U.S. Provisional Patent Application No. 61/677,593, filed Jul. 31, 2012, and U.S. Provisional Patent Application No. 61/676,641, filed Jul. 27, 2012, the entire disclosures of which are hereby incorporated by reference in their entirety.

FIELD OF THE INVENTION

This invention describes methods for performing a solution based assay reaction with an electroactive active moiety (EAM) that subsequently forms a self-assembled monolayer (SAM) utilizing the advantages of faster solution reaction kinetics, SAM protected electrode and surface based electrochemistry for electronic measurement.

BACKGROUND OF THE INVENTION

The electromotive force (EMF) is the maximum potential difference between two electrodes of a galvanic or voltaic cell, where the standard hydrogen electrode is on the left-hand side for the following cell:

| 1 | | | | 2 |
|---|---|---|---|---|
| Pt Electrode | $H_2$ | Aqueous Electrolyte Solution | $10^{-3}$ M Fe(ClO$_4$)$_3$ $10^{-3}$ M Fe(ClO$_4$)$_2$ | Pt |

The EMF is called the electrode potential of the electrode placed on the right-hand side in the graphical scheme of the cell, but only when the liquid junction between the solutions can be neglected or calculated, or if it does not exist at all.

The electrode potential of the electrode on the right-hand side (often called the oxidation-reduction potential) is given by the Nernst equation $$E_{Fe^{3+}/Fe^{2+}} = E_{Fe^{3+}/Fe^{2+}}^0 + (RT/F)\ln(a_{Fe^{3+}}/a_{Fe^{2+}})$$

This relationship follows from equation (2.21) when $(\mu_{Fe^{3+}}^0 - \mu_{Fe^{2+}}^0)/F$ is set equal to $E_{Fe^{3+}/Fe^{2+}}^0$ and the pH and $\ln p_{H_2}$ are equal to zero. In the subscript of the symbol for the electrode potential the symbols for the oxidized and reduced components of the oxidation-reduction system are indicated. With more complex reactions it is particularly recommended to write the whole reaction that takes place in the right-hand half of the cell after symbol E (the 'half-cell' reaction); thus, in the present case $$E_{Fe^{3+}/Fe^{2+}} \equiv E(Fe^{3+} + e = Fe^{2+})$$

Quantity $E_{Fe^{3+}/Fe^{2+}}^0$ is termed the standard electrode potential. It characterizes the oxidizing or reducing ability of the component of oxidation-reduction systems. With more positive standard electrode potentials, the oxidized form of the system is a stronger oxidant and the reduced form is a weaker reductant. Similarly, with a more negative standard potential, the reduced component of the oxidation-reduction system is a stronger reductant and the oxidized form a weaker oxidant.

The standard electrode $E^0$, in its standard usage in the Nernst equation, equation (1-2) is described as:

$$E = E^0 + \frac{2.3\, RT}{nF} \log \frac{C_O(0, t)}{C_R(0, t)}$$

where $E^0$ is the standard potential for the redox reaction, R is the universal gas constant (8.314 JK$^{-1}$ mol$^{-1}$), T is the Kelvin temperature, n is the number of electrons transferred in the reaction, and F is the Faraday constant (96,487 coulombs). On the negative side of $E^0$, the oxidized form thus tends to be reduced, and the forward reaction (i.e., reduction) is more favorable. The current resulting from a change in oxidation state of the electroactive species is termed the faradaic.

Previous work describes using conversion of functional groups attached to a transitional metal complex resulting in quantifiable electrochemical signal at two unique potentials, $E^0_1$ and $E^0_2$. See for example, U.S. Patent Publication Nos. US 2011 0033869 and US 2012-0181186, all herein incorporated by reference in their entirety. The methods generally comprise binding an analyte within a sandwich of binding ligands which may have a functional tag, on a solid support other than the electrode. After target binding, a peroxide generating moiety or an intermediary enzyme and substrate are added which generates hydrogen peroxide. The redox active complex is bound to an electrode and comprises a peroxide sensitive moiety (PSM). The peroxide generated from the enzyme system reacts with the PSM, removing a self-immolative moiety (SIM) and converting functional groups attached to a transitional metal complex resulting in quantifiable electrochemical signal at two unique potentials, $E^0_1$ and $E^0_2$.

SUMMARY OF THE INVENTION

The present invention provides composition and methods for the detection of target analytes by allowing the surrogate target, peroxide, to react in the solution phase with the redox active electro active moiety (EAM). In particular the peroxide reacts with the peroxide sensitive moiety (PSM) of an EAM, removing a self-immolative moiety (SIM) and converting functional groups attached to a transitional metal complex. Both the reacted and remaining unreacted EAMs are delivered to an electrode where a self-assembled monolayer is formed resulting in quantifiable electrochemical signal at two unique potentials, $E^0_1$ and $E^0_2$ when electrode is interrogated. In particular, the present invention discloses the advantages of executing the reaction between peroxide and the PSM of an EAM in the solution phase.

The surprising and unexpected benefit of the self-assembled monolayer in this disclosure is that it can be formed for the detection phase of the assay but is not required for the target interaction phase of the assay (e.g., binding) or the signal generation reaction (peroxide reacting with EAM). This is unique and unexpected as the conventional applications require that a self-assembled monolayers have a particular pre-determined state in which a change is detected in the presence of target. Another important characteristic of the method of the disclosure is that reacted and unreacted EAMs covalently bind to the electrode as similar rates. This is evidenced by the formation of a mixed SAM of reacted and unreacted EAM after peroxide has reacted with a portion of EAM provided. This method also provides a significant improvement to a reaction of target in solution and EAMs on an electrode surface.

In one aspect, the invention provides compositions and methods for the detection of target analyte in a test sample, said methods comprising (a) contacting a test sample and a capture binding ligand that binds to a target analyte, under conditions wherein said capture binding ligand binds said target analyte, if present, in said test sample to form a first complex, said capture binding ligand bound to a first solid support;

(b) contacting said first complex with a second binding ligand under conditions wherein said first complex and said second binding ligand bind to form a second complex, wherein said second binding ligand comprises an intermediary enzyme of a peroxide-generating system;

(c) isolating said second complex;

(d) contacting said second complex with a substrate for said intermediary enzyme of peroxide-generating system under conditions such that products are generated to form a first assay mixture;

(e) contacting a peroxide-generating enzyme with a first assay mixture under conditions wherein peroxide is generated to form a peroxide-containing second assay mixture;

(f) contacting said peroxide containing second assay mixture with said electroactive moiety (EAM) comprising a transition metal complex, a self-immolative moiety (SIM), and a peroxide sensitive moiety (PSM), wherein said SIM joins the PSM to the transition metal complex and wherein said EAM has a first $E^0$, to form a third assay mixture wherein said peroxide reacts in the solution phase with said PSM of said EAM to release said SIM from said EAM and result in said EAM having a second $E^0$;

(g) contacting said third assay mixture with a second solid support comprising an electrode under conditions such that a covalently attached self-assembled monolayer (SAM) forms comprising said EAM with said first $E^0$ and with said second $E^0$; and (h) detecting for a change between the first $E^0$ and the second $E^0$ of said EAM, wherein said change is an indication of the presence of said target analyte.

In another aspect, the disclosure provides methods for detecting a target analyte in a test sample, said method comprising:

(a) contacting said target analyte with a peroxide-generating enzyme, under conditions wherein said target, if present, acts as a substrate for said peroxide-generating enzyme and peroxide is generated forming a first assay mixture;

(b) contacting said peroxide-containing first assay mixture with an electroactive moiety (EAM), said EAM comprising a transition metal complex, a self-immolative moiety (SIM), and a peroxide sensitive moiety (PSM), wherein said SIM joins the PSM to the transition metal complex and wherein said EAM has a first $E^0$ to form a second assay mixture wherein said peroxide reacts in the solution phase with said PSM of said EAM to release said SIM from said EAM and result in said EAM having a second $E^0$;

(c) contacting said second assay mixture with a first solid support comprising an electrode under conditions that a covalently attached self-assembled monolayer (SAM) forms comprising said EAM with said first $E^0$ and with said second $E^0$;

(d) detecting for a change between the first $E^0$ and the second $E^0$ of said EAM, wherein said change is an indication of the presence of said target analyte.

In one embodiment of the disclosure any preceding embodiment is where the target analyte is a protein. In another embodiment of the disclosure any preceding embodiment is where the target is a small molecule.

In one embodiment of the disclosure any preceding embodiment where said first solid support is chosen from the group consisting of microparticles, magnetic microparticles, beads, microchannels or membranes.

In one embodiment of the disclosure any preceding embodiment where said product(s) is a substrate for said peroxide-generating enzyme.

In one embodiment of the disclosure any preceding embodiment further comprises the presence of a substrate for said peroxide-generating enzyme and wherein said product(s) is a cofactor for said peroxide-generating enzyme.

In one embodiment of the disclosure any preceding embodiment said intermediary enzyme of a peroxide-generating system is alkaline phosphatase (AP) or any other dephosphorylating enzyme.

In another embodiment of the disclosure any preceding embodiment is where said peroxide-generating enzyme is selected from the group consisting of D-amino acid oxidase (DAAO), or any flavin dependent oxidoreductase enzyme.

In one embodiment of the disclosure any preceding embodiment is where said intermediary enzyme of a peroxide generating system is an oxidase enzyme, including glucose oxidase.

In another embodiment of the disclosure any preceding embodiment is where said first binding ligand and said second binding ligand are independently chosen from the group consisting of monoclonal antibodies, fragments of monoclonal antibodies, polyclonal antibodies, fragments of polyclonal antibodies, proteins, and peptides.

In one embodiment of the disclosure any preceding embodiment is where said peroxide is hydrogen peroxide ($H_2O_2$).

In one embodiment of the disclosure any preceding embodiment is where said EAM comprises a transition metal. In another embodiment, said transition metal is chosen from the group consisting of iron, ruthenium and osmium.

In one embodiment of the disclosure any preceding embodiment is said EAM is chosen from the group consisting of ferrocene and substituted ferrocene.

DETAILED DESCRIPTION OF THE INVENTION

Overview

Figure 1:
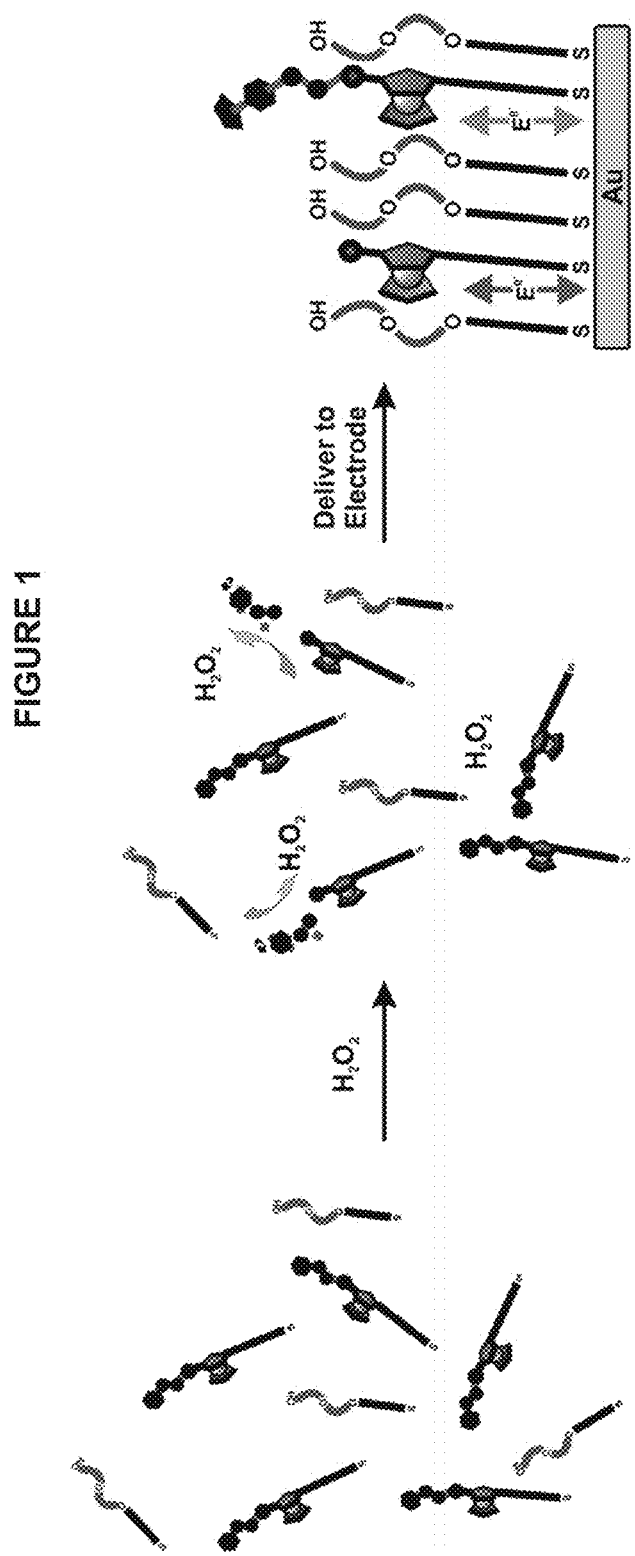
FIG. 1 illustrates a homogeneous, solution based reaction, assay scheme.

This invention describes a method for performing a solution based target (surrogate target)-EAM reaction and a SAM based detection of that EAM on an electrode. This assay technique utilizes the advantages of solution based reaction kinetics over solution-surface or solution-monolayer reaction rates.

This invention describes the homogeneous reaction of a PSM (as defined below) with peroxide in solution, where the concentration of peroxide that is generated is dependent on the concentration of the target analyte. Then the reacted and remaining unreacted PSM, with other components, form a self-assembled monolayer (SAM) on an electrode for subsequent electronic measurements.

One of the challenges confronting current Point-of-Care assays is reduced sample-to-result time without sacrificing performance or increasing cost. Increasing reagent concentration is costly and does not necessarily translate to a faster assay. Generally, sensitivity is directly dependent on time, for one or more steps of an assay, and therefore decrease time inherently impacts performance. Increasing the reaction rate of any or all steps of an assay is critical to reducing total assay time without sacrificing performance. This invention provides a means to increase the reaction rate between the target (or surrogate target) and the detection molecules without increasing reagent concentration or adding unmanageable complexity. The increase in the reaction rate is possible by taking advantage of the diffusion kinetics of a solution based reaction compared to a surface based reaction. Furthermore, higher signal levels provide more differentiation between target (or surrogate target) concentrations which allows for greater assay sensitivity.

Advantages of this solution based reaction extend to manufacturing as well. With the traditional surface, monolayer-based setup, solution must be pre-spotted onto an electrode and SAM formation allowed to occur. Generally to obtain the necessary throughput this is done with a large, expensive commercial spotter. Additionally, another challenge to this manufacturing method is accessibility of electrode for spotting inside a fluidic cartridge or the incorporation of modified electrode into a fluidic cartridge without damaging the SAM on the electrode surface. These manufacturing challenges add complexity and cost to a disposable detection card. Utilizing the solution based EAM-target (or surrogate target) requires no electrode pre-modification and the EAM and other SAM components can be stored as a reagent used in situ on the detection card.

The sensitivities and timing of enzyme-triggered redox altering chemical elimination (E-TRACE) assays for proteins, DNA, and small molecules may be enhanced through a homogeneous, solution based reaction of surrogate target hydrogen peroxide and EAM molecules as described herein. E-TRACE technology is previously described in U.S. Patent Publication No. US 20120181186, filed Jan. 19, 2012 which claims the benefit of priority to U.S. provisional application Nos. 61/434,122, filed Jan. 19, 2011 and 61/523,679, filed Aug. 15, 2011 and Ser. No. 12/853,204, filed Aug. 9, 2010, which claims the benefit of priority to U.S. provisional application Nos. 61/232,339, filed Aug. 7, 2009, and in U.S. patent application Ser. No. 13/653,931, filed Oct. 17, 2012, all which are incorporated by reference in their entirety.

In one embodiment, the target analyte is contacted directly with the peroxide-generating enzyme under conditions such that the target, if present, acts as a substrate for the peroxide-generating enzyme and peroxide is generated, forming a first assay mixture. This first assay mixture is then contacted with the EAM having a first $E^o$ to produce a second assay mixture. The peroxide reacts with the EAM to release said SIM from the EAM to generate an EAM having a second $E^o$. The second assay mixture is then contacted with a first solid support comprising an electrode under conditions such that a SAM comprising said EAM having a first $E^o$ and said EAM having a second $E^o$ is formed. The difference between the first $E^o$ and the second $E^o$ of the EAM is detected, and if such a change occurs, it is an indication of the presence of the target analyte.

An exemplary method for a homogeneous, solution based reaction, assay is shown in FIG. 1. Direct peroxide interaction with PSM is performed in solution. Any of the E-TRACE EAMs comprising an immolative head group, Ferrocene, anchor, and thiol group can be utilized in this format as the detection molecule for hydrogen peroxide ($H_2O_2$).

Step 1: Reaction—addition of a target solution to an EAM solution

Step 2: SAM Growth—delivery of EAM/Target solution to an electrode for SAM growth Step 3: Wash and Test—washing of the electrode, addition of testing solution, and performing electrochemical measurements.

The assay relies on the use of an electroactive moiety ("EAM"), which comprises a self-immolative moiety, whose presence gives the EAM a first $E^o$, whose absence, upon irreversible cleavage, gives the EAM a second $E^o$.

In another embodiment, the assay also relies on a capture binding ligand attached to a solid support that will bind the target analyte upon its introduction to form a first complex. A soluble second binding ligand is introduced, which also binds the first complex to form a second complex. The second binding ligand comprises an intermediary enzyme of a peroxide generating system, such as an Alkaline Phosphatase enzyme system. The second complex is isolated and optionally washed with a suitable buffer. Upon the addition of oxygen and a substrate for the intermediary enzyme of the peroxidase generating system (e.g., flavin adenine dinucleotide phosphate (FADP) for the alkaline phosphatase as the intermediary enzyme) such that products are generated from the intermediary enzyme to form a first assay mixture. As defined here, products include flavin adenine dinucleotide (FAD) and a free phosphate. A peroxide-generating enzyme is then contacted with the first assay mixture and a substrate for said peroxide generating enzyme wherein peroxide is generated and a second assay mixture is produced. The second assay mixture is contacted with the EAM, wherein the peroxide attacks the self-immolative moiety and causes the removal of the self-immolative moiety from the EAM, which in turn results in a change in the $E^o$ of the EAM, forming a third assay mixture. The third assay mixture is then contacted with a second solid support under conditions such that a SAM comprising said EAM having a first $E^o$ and said EAM having a second $E^o$ is formed. The difference between the signal magnitude at the first $E^o$ and the second $E^o$ of the EAM is detected, and if such a change occurs, it is an indication of the presence of the target analyte.

Thus, to determine whether a target analyte is present in the sample, the sample is applied to the solid support comprising a capture binding ligand, optionally washed, and an oxidase enzyme-conjugated secondary binding ligand (for example, an antibody) that binds an alternative epitope of the target analyte is added, creating a "sandwich assay" format with the target. The surface is optionally washed, and treated with an oxygen-saturated buffer containing a high concentration of glucose. The presence of the substrate oxidase enzyme (sometimes referred to herein as "SOX" e.g. glucose oxidase) on the surface results in the enzymatic creation of hydrogen peroxide in solution. This peroxide containing solution is then mixed with the EAM in solution, triggering a chemical elimination reaction ("self-immolative" reaction) in the solution phase EAMs. This irreversible elimination reaction changes the electronic environment of the EAM, for example by altering the "R" groups (e.g., substituent groups) of the transition metal complex, thus shifting the apparent formal potential of the EAM to a second $E^0$ to signal the presence of the target. The peroxide and EAM containing solution is then delivered to an electrode where EAMs react with the electrode surface forming a self-assembled monolayer. The first and second $E^0$, of both reacted and unreacted EAMS is then measured electrochemically as an indication of the amount or presence of target analyte.

Figure 6:
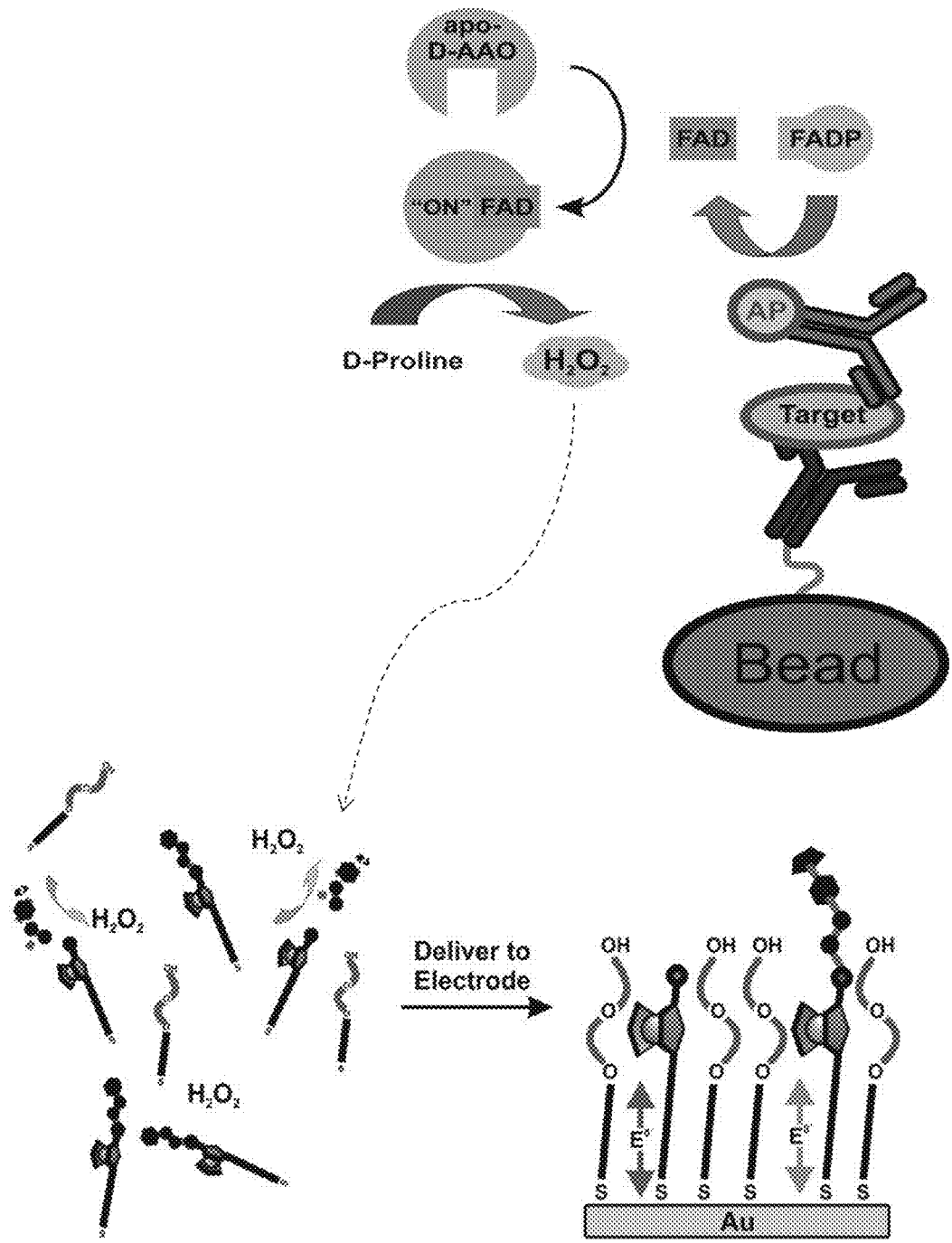
FIG. 6 illustrates generic protein assay using enzymatic signal amplification and solution based peroxide and EAM reaction.
Figure 7:
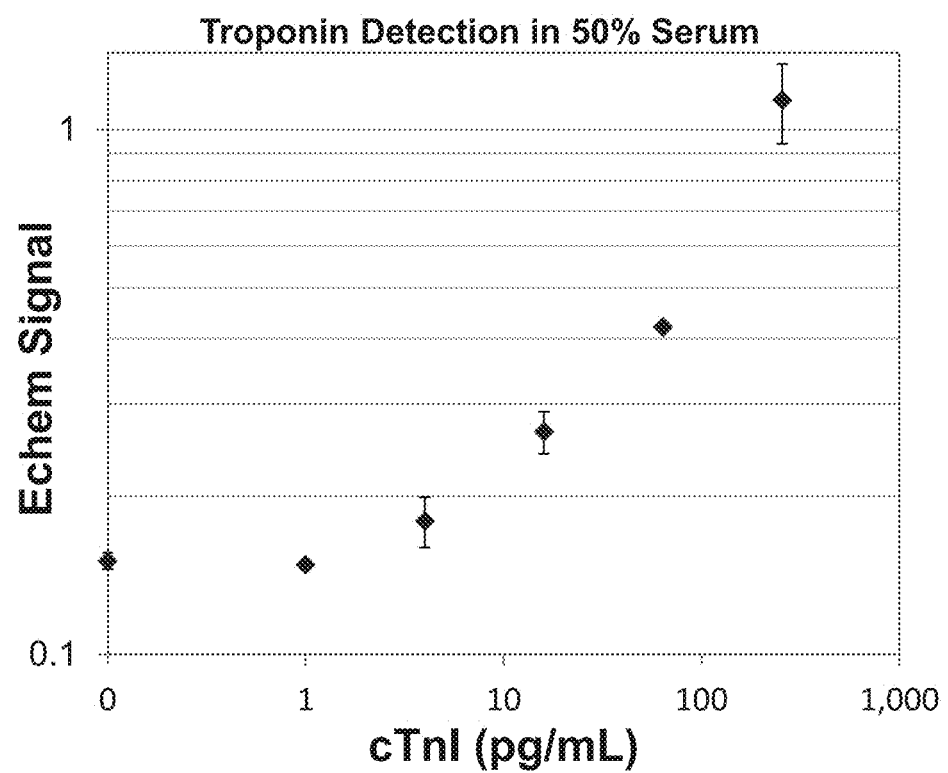
FIG. 7 shows a dose response for a 15-minute troponin assay using solution based peroxide and EAM reaction.

Additionally this invention describes applications of target detection utilizing signal amplification strategies that rely on target-dependent enzyme cascades for generating hydrogen peroxide. FIG. 6 shows a general approach for cascade signal amplification based on an alkaline phosphatase (AP)-tagged sandwich immunocomplex with a protein target. A similar colorimetric assay has been reported previously (Li et al., Current Medicinal Chemistry 8 (2001), p. 121-133). In this system the soluble capture ligand comprising alkaline phosphatase, catalyzes the dephosphorylation of FADP to yield FAD, an enzyme cofactor that turns "on" a dormant apo-D-amino acid oxidase (D-AAO). In turn, each active D-AAO generated oxidizes D-proline and produces hydrogen peroxide which is detected using the Ohmx E-TRACE technology, which is described in U.S. Patent Publication No. US 20120181186, filed Jan. 19, 2012 which claims the benefit of priority to U.S. provisional application Nos. 61/434,122, filed Jan. 19, 2011 and 61/523,679, filed Aug. 15, 2011 and Ser. No. 12/853,204, filed Aug. 9, 2010, which claims the benefit of priority to U.S. provisional application Nos. 61/232,339, filed Aug. 7, 2009, and in U.S. patent application Ser. No. 13/653,931, filed Oct. 17, 2012, all which are incorporated by reference in their entirety. An example protein target detected in this manner is shown in FIG. 7, where a dilution series of cardiac troponin-I (cTnI) in serum is analyzed. The data suggest a detection limit below the pg/mL regime is possible for cTnI in serum using this homogeneous, solution based, E-TRACE assay.

An exemplary troponin assay process includes the following steps: (a) binding of target to antibody-coated beads; (b) binding of biotin-secondary antibody to target; (c) binding of streptavidin-AP to target antibody complex; (d) amplifying signal; (e) contacting for time sufficient to react with monolayer components; and (f) SAM formation for detection.

Accordingly, the present invention provides methods and compositions for detecting target analytes in samples. In a particular application a single measurement approach for detecting directly the percentage of glycated Hemoglobin is described where the measurement is not affected by the amount of total Hemoglobin present in the sample. Since total Hemoglobin, can vary physiologically from 5-20 g/dL, a direct measurement of the same percentage of glycated Hemoglobin across this range is feasible with this approach.

Target Analytes

By "target analyte" or "analyte" or "target" or grammatical equivalents herein is meant any molecule, compound or particle to be detected. Target analytes bind to binding ligands (both capture and soluble binding ligands), as is more fully described below.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc.

In some embodiments, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including anti-eptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g., respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella zoster virus, cytomegalovirus, Epstein Barr virus), rotaviruses, Norwalk viruses, hantavirus, arenavirus, rhabdovirus (e.g. rabies virus), retroviruses (including HIV, HTLV I and II), papovaviruses (e.g. papillomavirus), polyomaviruses, and picornaviruses, and the like), and bacteria (including a wide variety of pathogenic and non-pathogenic prokaryotes of interest including *Bacillus*; *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis, M. leprae*; *Clostridium*, e.g. *C. botulinum, C. tetani, C. difficile, C. perfringens*; *Cornyebacterium*, e.g. *C. diphtheriae*; *Streptococcus, S. pyogenes, S. pneumoniae*; *Staphylococcus*, e.g. *S. aureus*; *Haemophilus*, e.g. *H. influenzae*; *Neisseria*, e.g. *N. meningitidis, N. gonorrhoeae*; *Yersinia*, e.g. *G. lamblia Y. pestis, Pseudomonas*, e.g. *P. aeruginosa, P. putida*; *Chlamydia*, e.g. *C. trachomatis*; *Bordetella*, e.g. *B.*

*pertussis; Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone, testosterone; and (4) other proteins (including α-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

Targets include small molecules such as glucose or cholesterol or ATP, FADP, NADH and other metabolites, or hormones (such as testosterones etc.), or proteins (such as thyroid stimulating hormone, troponin I etc.)

In one embodiment, a single measurement method for determining the proportion of target analyte in a sample can be performed according to the methods described herein by an electrochemical measurement using the inventive enzyme-triggered redox altering chemical elimination (E-TRACE) reaction, or a standard immunoassay optical test detecting $H_2O_2$ in solution and is described in the following steps:

Step 1: Modification with primary antibody: A solid support is modified with a capture probe. This capture probe, e.g., antibody, binds selectively and equivalently to all variant types of target (e.g., hemoglobin including hemoglobin and glycated hemoglobin). As defined herein, the terms "binds selectively" means binding to a predetermined target (e.g. total hemoglobin including glycated hemoglobin (hemoglobin A1c)) and "binds equivalently" mean non-preferentially to both the protein (e.g., hemoglobin) and the glycated protein (e.g., hemoglobin A1c).

Step 2: Addition of target: Target can be small molecule or protein. In certain embodiments, the primary binding occurs and is assumed to saturate nearly all binding sites on the surface of the secondary support. The importance of this is that samples with different total target concentrations will still yield a representative proportion of the target analyte bound to the surface.

Step 3: Addition of detection antibody: In certain embodiments, the secondary antibody is introduced to the surface and only binds to the immobilized target analyte. This means the ELISA-like sandwich complex only forms on sites occupied by target analyte and not on sites occupied by non-target (e.g., non-glycated hemoglobin).

Step 4: Signal transduction and detection: The anti-target antibody that selectively binds to target is labeled with an intermediary enzyme of a peroxide generating system, e.g., an oxidase enzyme (SOx). The intermediary enzyme label generates a product that is a cofactor or substrate for an oxidase enzyme which produces hydrogen peroxide. The redox active EAM is delivered to the hydrogen peroxide containing assay mixture and reaction between the PSM of the EAM and the hydrogen peroxide proceeds homogeneously in the solution phase.

Step 5: SAM formation: Combing assay mixture of hydrogen peroxide reacted and unreacted EAM is delivered to an unmodified electrode where SAM formation of both reacted and unreacted EAM occurs. Quantifiable signal of both reacted and unreacted EAM can then be measured The amount of signal is directly correlated to the number of sandwich complexes, which in turn is dependent on how much hemoglobin A1c is immobilized on the surface. Since the amount of immobilized hemoglobin A1c is directly dependent on the percentage of hemoglobin A1c is to total hemoglobin in the original sample, the signal observed provides an assessment of the ratio (percentage) of hemoglobin A1c to total hemoglobin.

For hemoglobin A1c is, one of the binding ligands, either the capture binding ligand or the soluble binding ligand has specificity for the glycated form of hemoglobin. That is, in one embodiment, the capture binding ligand can bind either form of hemoglobin; after washing the surface, a soluble binding ligand that has specificity only for the glycated form (i.e. Hb A1c) with the peroxide-generating moiety is added. Alternatively, the capture binding ligand has specificity for Hb1Ac over other forms of hemoglobin, and a soluble capture ligand without such specificity can be used after appropriate washing of the surface. This approach can be used for other target analytes where detection of either the glycated or non-glycated form is desired. As will be appreciated by those in the art, there are also target analytes for which detection of both forms is desired, and in those embodiments, using binding ligands that do not have specificity for one or the other is used.

This single-measurement detection of hemoglobin A1c is coupled to an electro-active SAM provides a less complex means for determining the proportion of Target to total hemoglobin in a sample. It offers the advantages of not needing to perform two measurements, as well as eliminating optical measurements, multiple antibody pairs, or percentage calculation algorithms, that introduces further error, based on two separate measurements for hemoglobin A1c is and total hemoglobin Target analytes of the disclosure may be labeled. Thus, by "labeled target analyte" herein is meant a target analyte that is labeled with a member of a specific binding pair.

Samples

The target analytes are generally present in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples, purified samples, raw samples, etc.; as will be appreciated by those in the art, virtually any experimental manipulation may have been done on the sample. Some embodiments utilize target samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage.

Solid Supports

The target analytes are detected using solid supports comprising electrodes. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with printed circuit board (PCB) materials being particularly preferred. In one embodiment, solid support is selected from microparticles, magnetic microparticles, beads, and microchannels.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer. Accordingly, in a preferred embodiment, the present invention provides chips that comprise substrates comprising a plurality of electrodes, preferably gold electrodes. The number of electrodes is as outlined for arrays. Each electrode becomes modified with a self-assembled monolayer in situ during the last step of the assay as outlined herein. In addition, each electrode has an interconnection, that is the electrode is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety).

Electrodes

The solid supports of the invention comprise electrodes. By "electrodes" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide (Mo2O6), tungsten oxide (WO3) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used.

The electrodes of the invention are generally incorporated into cartridges and can take a wide variety of configurations, and can include working and reference electrodes, interconnects (including "through board" interconnects), and microfluidic components. See for example U.S. Pat. No. 7,312,087, incorporated herein by reference in its entirety. In addition, the chips generally include a working electrode with the components described herein, a reference electrode, and a counter/auxiliary electrode.

In a preferred embodiment, detection electrodes consist of an evaporated gold circuit on a polymer backing.

The cartridges include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

Self-Assembled Monolayers

The electrodes comprise a self-assembled monolayer ("SAM") formed in situ as part of the assay. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. In addition, a monolayer serves to keep charge carriers away from the surface of the electrode.

In some embodiments, the monolayer comprises conductive oligomers, and in particular, conductive oligomers are generally used to attach the EAM to the electrode surface, as described below. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electro-active polymers, that themselves may donate or accept electrons.

A more detailed description of conductive oligomers is found in WO/1999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

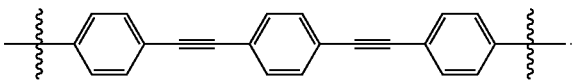

In addition, the terminus of at least some of the conductive oligomers in the monolayer is electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, in a preferred embodiment, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —NH, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

The passivation agents thus serve as a physical barrier to block solvent accessibility to the electrode. As such, the passivation agents themselves may in fact be either (1) conducting or (2) nonconducting, i.e. insulating, molecules. Thus, in one embodiment, the passivation agents are conductive oligomers, as described herein, with or without a terminal group to block or decrease the transfer of charge to the electrode. Other passivation agents which may be conductive include oligomers of —(CF$_2$)$_n$—, —(CHF)$_n$— and —(CFR)$_n$—. In a preferred embodiment, the passivation agents are insulator moieties.

In some embodiments, the monolayers comprise insulators. An "insulator" is a substantially nonconducting oligomer, preferably linear. By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —(CH$_2$)$_{16}$ molecules, still may transfer electrons, albeit at a slow rate.

In some embodiments, the insulators have a conductivity, S, of about $10^{-7}$ Ω–1 cm$^{-1}$ or lower, with less than about $10^{-8}$ Ω$^{-1}$ cm$^{-1}$ being preferred. Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer. In some embodiments the insulator comprises C$_6$-C$_{16}$ alkyl.

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the analyte, etc. For example, there may be charged groups on the terminus to form a charged surface to encourage or discourage binding of certain target analytes or to repel or prevent from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them.

The in situ monolayer may comprise a single type of passivation agent, including insulators, or different types.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, i.e. nitrogen or sulfur (sulfur derivatives are not preferred when the electrode is gold). In some embodiments, the insulator comprises C$_6$ to C$_{16}$ alkyl.

In some embodiments, the electrode is a metal surface and need not necessarily have interconnects or the ability to do electrochemistry.

Electroactive Moieties

In addition to the SAMs, the in situ modified electrodes comprise an EAM. By "electroactive moiety (EAM)" or "transition metal complex" or "redox active molecule" or "electron transfer moiety (ETM)" herein is meant a metal-containing compound which is capable of reversibly or semireversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention. Metals that find use in the invention also are those that do not change the number of coordination sites upon a change in oxidation state, including ruthenium, osmium, iron, platinium and palladium, with osmium, ruthenium and iron being especially useful. Generally, transition metals are depicted herein (or in incorporated references) as TM or M.

The transitional metal and the coordinating ligands form a metal complex. By "ligand" or "coordinating ligand" (depicted herein or in incorporated references in the figures as "L") herein is meant an atom, ion, molecule, or functional group that generally donates one or more of its electrons through a coordinate covalent bond to, or shares its electrons through a covalent bond with, one or more central atoms or ions.

In some embodiments, small polar ligands are used; suitable small polar ligands, generally depicted herein as "L", fall into two general categories, as is more fully described herein. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Some of the structures of transitional metal complexes are shown below:

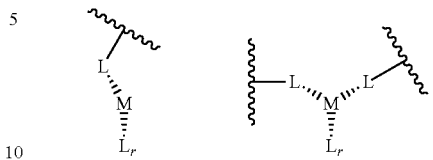

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e., the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as Lm). Suitable nitrogen donating ligands are well known in the art and include, but are not limited to, cyano (C≡N), NH$_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

As will be appreciated in the art, any ligand donor(1)-bridge-donor(2) where donor (1) binds to the metal and donor (2) is available for interaction with the surrounding medium (solvent, protein, etc.) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N═C═O), thiocyanates, isonitrile, $N_2$, $O_2$, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has particular advantages over the others because it is more inert, easier to prepare, more favorable reduction potential. Generally that a larger CN/L ratio will give larger shifts.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In some embodiments, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with .pi.-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [$C_5H_5$ (−1)] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [$(C_5H_5)_2$ Fe] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example. Other acyclic π-bonded ligands such as the allyl(−1) ion, or butadiene yield potentially suitable organometallic compounds, and all such ligands, in conduction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

As a general rule, EAM comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocylic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

In some embodiments, a mixture of monodentate (e.g., at least one cyano ligand), bi-dentate, tri-dentate, and polydentate ligands can be used in the construction of EAMs.

Of particular use in the present invention are EAMs that are metallocenes, and in particular ferrocenes, which have at least a first self-immolative moiety attached, although in some embodiments, more than one self-immolative moiety is attached as is described below (it should also be noted that other EAMs, as are broadly described herein, with self-immolative moieties can also be used). In some embodiments, when more than one self-immolative moiety is attached to a ferrocene, they are all attached to one of the cyclopentydienyl rings. In some embodiments, the self-immolative moieties are attached to different rings. In some embodiments, it is possible to saturate one or both of the cyclopentydienyl rings with self-immolative moieties, as long as one site is used for attachment to the electrode.

In some embodiments, the EAMs comprise substituted 1,1'-ferrocenes. Ferrocene is air-stable. It can be easily substituted with both capture ligand or reactive moiety and anchoring group. Upon binding of the target protein to the capture ligand on the ferrocene which will not only change the environment around the ferrocene, but also prevent the cyclopentadienyl rings from spinning, which will change the energy by approximately 4kJ/mol. WO/1998/57159; Heinze and Schlenker, Eur. J. Inorg. Chem. 2974-2988 (2004); Heinze and Schlenker, Eur. J. Inorg. Chem. 66-71 (2005); and Holleman-Wiberg, Inorganic Chemistry, Academic Press 34th Ed, at 1620, all incorporated by reference.

known (see, Bickert et al., *Organometallics* 1984, 3, 654-657; Farrington et al., *Chem. Commun.* 2002, 308-309; Pichon et al., *Chem. Commun.* 2004, 598-599; and Steurer et al., *Organometallics* 2007, 26, 3850-3859), electrochemical studies of this class of molecules in SAMs have not been reported in the literature. In contrast to 1,1'-disubstituted ferrocenes where cyclopentadienyl (Cp) ring rotation can place both Cp substituents in an eclipsed conformation, 1,3-disubstituted ferrocene regioisomers provide a molecular architecture that enforces a rigid geometry between these Cp groups. Representative examples of 1,3-disubstitued ferrocenes are shown below such as compounds 1-5. An example of a 1,3-disubstituted ferrocene for attaching both anchoring and functional ligands is shown below:

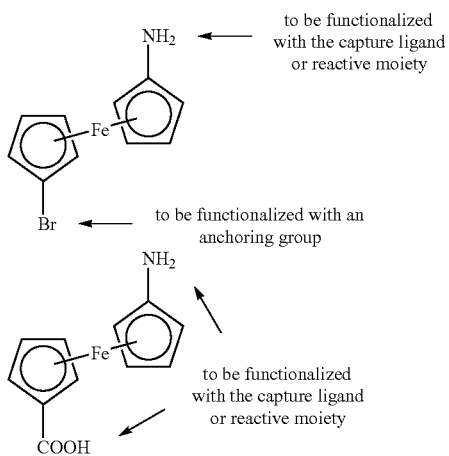

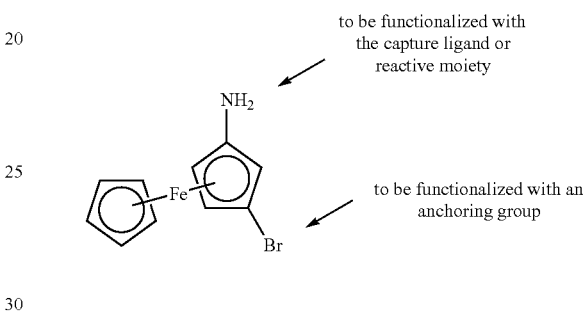

In some other embodiments, the EAMs comprise 1,3-disubstituted ferrocenes. While 1,3-disubstituted ferrocenes are A series of 1,3-disubstituted ferrocene derivatives (1-4) were synthesized with different functional moieties and organosulfur anchoring groups for SAM formation on gold, and are shown below.

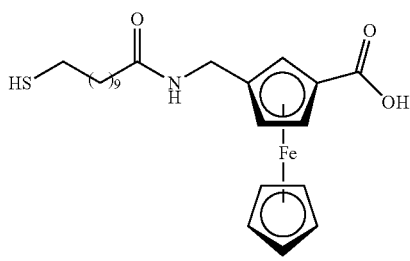

1

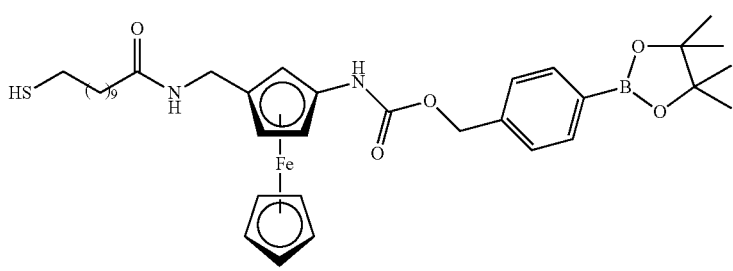

2

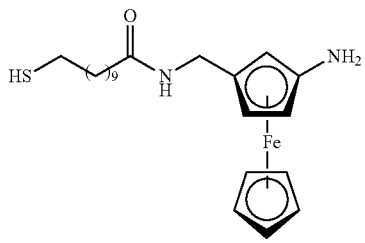

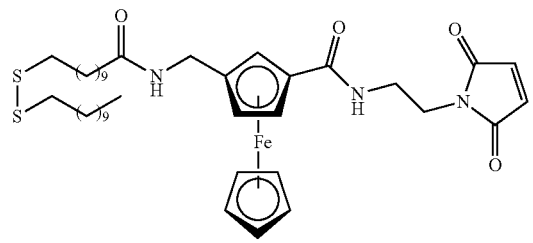

-continued

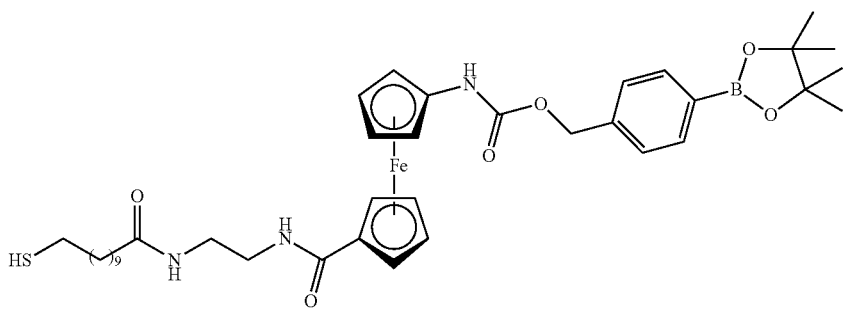

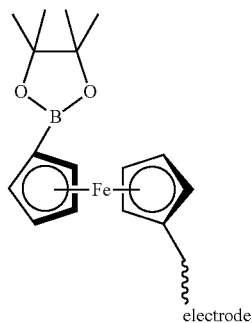

electrode

Additional ferrocene EAMs suitable for use in methods of disclosure are disclosed in U.S. patent application Ser. No. 13/667,713, filed Nov. 2, 2012, which claims the benefit of U.S. Provisional Application No. 61/555,945, filed Nov. 4, 2011, all which are expressly incorporated by reference in their entirety.

Figure 8:
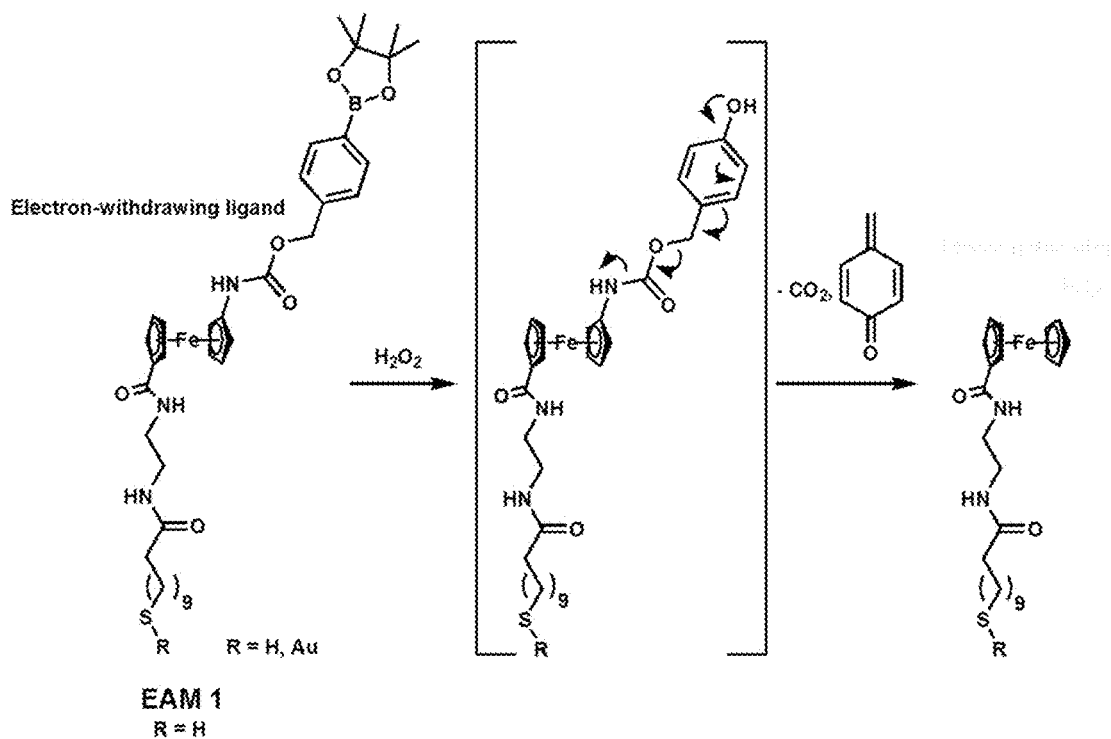
FIG. 8 illustrates structure of electroactive molecule (EAM) 1 and mechanism of peroxide-induced ligand dissociation. The change in ligand electronics is responsible for the shift in redox potential.

In addition, EAMs generally have an attachment moiety for attachment of the EAM to the conductive oligomer which is used to attach the EAM to the electrode. In general, although not required, in the case of metallocenes such as ferrocenes, the self-immolative moiety(ies) are attached to one of the cyclopentydienyl rings, and the attachment moiety is attached to the other ring, as is generally depicted in FIG. 8, although attachment to the same ring can also be done. As will be appreciated by those in the art, any combination of self-immolative moieties and at least one attachment linker can be used, and on either ring.

In addition to the self-immolative moiety(ies) and the attachment moiety(ies), the ferrocene can comprise additional substituent groups, which can be added for a variety of reasons, including altering the $E^o$ in the presence or absence of at least the self-immolative group. Suitable substituent groups, frequently depicted in associated and incorporated references as "R" groups, are recited in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; and U.S. Provisional Patent Application No. 61/366,013, filed Jul. 20, 2010, hereby incorporated by reference.

In some embodiments, such as depicted below, the EAM does not comprise a self-immolative moiety, in the case where the peroxide-sensitive moiety is attached directly to the EAM and provides a change in $E^o$ when the peroxide-sensitive moiety is exposed to peroxide. As shown below, one embodiment allows the peroxide-sensitive moiety to be attached directly to the EAM (in this case, a ferrocene), such that the ferrocene has a first $E^o$ when the pinacol boronate ester moiety is attached, and a second $E^o$ when removed, e.g., in the presence of the peroxide.

Self-Immolative Moieties

The EAMs of the invention include at least one self-immolative moiety that is covalently attached to the EAM such that the EAM has a first $E^o$ when it is present and a second $E^o$ when it has been removed as described below.

The term "self-immolative spacer" refers to a bifunctional chemical moiety that is capable of covalently linking two chemical moieties into a normally stable tripartate molecule. The self-immolative spacer is capable of spontaneously separating from the second moiety if the bond to the first moiety is cleaved. In the present invention, the self-immolative spacer links a peroxide sensitive moiety, e.g., a boron moiety, to the EAM. Upon exposure to peroxide, the boron moiety is removed and the spacer falls apart, as generally depicted in FIG. 8. Generally speaking, any spacer where irreversible repetitive bond rearrangement reactions are initiated by an electron-donating alcohol functional group (i.e. quinone methide motifs) can be designed with boron groups serving as triggering moieties that generate alcohols under oxidative conditions. Alternatively, the boron moiety can mask a latent phenolic oxygen in a ligand that is a pro-chelator for a transition metal. Upon oxidation, the ligand is transformed and initiates EAM formation in the SAM. For example, a sample chelating ligand is salicaldehyde isonicotinoyl hydrazone that binds iron.

As will be appreciated by those in the art, a wide variety of self-immolative moieties may be used with a wide variety of EAMs and peroxide sensitive moieties. Self-immolative linkers have been described in a number of references, including US Publication Nos. 20090041791; 20100145036 and U.S. Pat. Nos. 7,705,045 and 7,223,837, all of which are expressly incorporated by reference in their entirety, particularly for the disclosure of self-immolative spacers.

Figure 9:
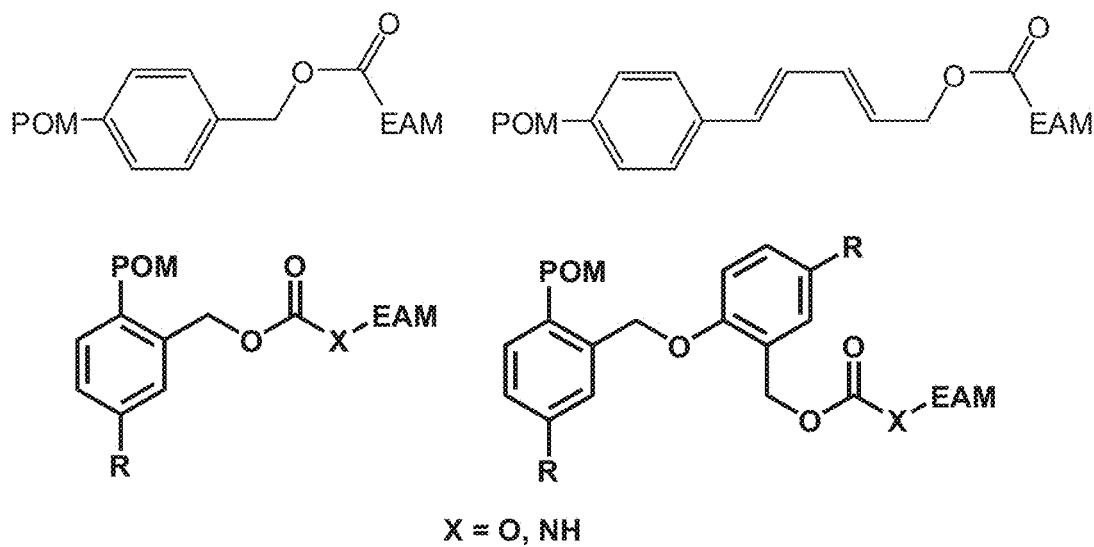
FIG. 9 Illustrates a sample self-immolative spacer groups based on substituted quinone methides.

A few self-immolative linkers of particular use in the present invention are shown in FIG. 9. The self-immolative spacer can comprise a single monomeric unit or polymers, either of the same monomers (homopolymers) or of different monomers (heteropolymers). Alternatively, the self-immolative spacer can be a neighboring group to an EAM in a SAM that changes the environment of the EAM following cleavage analogous to the chemistry as recited in previous application "Electrochemical Assay for the Detection of Enzymes", U.S. Ser. No. 12/253,828, PCT/US2008/080363, hereby incorporated by reference.

Peroxide Sensitive Moieties

The self-immolative spacers join the peroxide sensitive moieties (PSMs, sometimes referred to herein as POMs) and the EAMs of the invention. In general, a peroxide sensitive moiety is one containing boron, as depicted in FIG. 8.

For example, the figures herein depict the use of ferrocene derivatives, where the peroxide triggers a change from a benzyl carbamate with a p-substituted pinacol borate ester to an amine. This self-eliminating group has been described previously for generating amine-functionalized florophores in the presence of hydrogen peroxide (Sella, E.; Shabat, D. Self-immolative dendritic probe for the direct detection of triacetone triperoxide. Chem. Commun. 2008, 5701-5703; and Lo, L.—Cl; Chu, C.—Y. Development of highly selective and sensitive probes for hydrogen peroxide. Chem. Commun. 2003, 2728-2729 both of which are incorporated by reference. Other such groups (aryl borate esters and arylboronic acids) are also described in Sella and Lo. In addition, ferrocenylamines are known to exhibit redox behavior at lower potentials (~150 mV) as compared to their corresponding carbamate derviatives (see Sagi et al., Amperometric Assay for Aldolase Activity; Antibody-Catalyzed Ferrocenylamine Formation. Anal. Chem. 2006, 78, 1459-1461, incorporated by reference herein).

Capture and Soluble Binding Ligands

In addition to SAMs and EAMs, in some embodiments, a solid support comprises capture binding ligands. "Binding ligand" or "binding species" herein is meant a compound that is used to probe for the presence of the target analyte and that will bind to the target analyte. In general, for most of the embodiments described herein, there are at least two binding ligands used per target analyte molecule; a "capture" or "anchor" binding ligand that is attached to a solid support, and a soluble binding ligand, that binds independently to the target analyte, and either directly or indirectly comprises at least one label such as a SOX or intermediary enzyme of a peroxide generating system. By "capture binding ligand" herein is meant a binding ligand that binds the target analyte that is attached to a solid support that binds the target analyte. By "soluble binding ligand" herein is meant a binding ligand that is in solution that binds the target analyte at a different site than the capture binding ligand.

As will be appreciated by those in the art, the composition of the binding ligand will depend on the composition of the target analyte. Binding ligands for a wide variety of analytes are known or can be readily found using known techniques. For example, when the analyte is a protein, the binding ligands include proteins (particularly including antibodies or fragments thereof (FAbs, etc.)) or small molecules.

In general, antibodies are useful as both capture and soluble binding ligands.

The soluble binding ligand also comprises a peroxide generating moiety such as an enzyme that generates peroxide. As defined herein, the term "peroxide generating system" or "peroxide-generating system" means one or more enzymes that directly generates a peroxide from its substrate and/or an intermediary enzyme that generates an intermediate, e.g., a cofactor or pre-substrate, for another enzyme that in turn generates a peroxide. In one example, a peroxide generating moiety may be an enzyme that generates peroxide, e.g., "peroxide generating enzyme". A wide variety of such enzymes are known, including glucose oxidase, acyl CoA oxidases, alcohol oxidases, aldehyde oxidases, etc. A wide variety of suitable oxidase enzymes are known in the art (see any glucose oxidase enzyme classified as EC 1.1.3.4, including, but not limited to, glucose oxidase, D-amino acid oxidase (DAAO) and choline oxidase). Glucose oxidase enzymes from a wide variety of organisms are well known, including bacterial, fungal and animal (including mammalian), including, but not limited to, *Aspergillus* species (e.g. *A. niger*), *Penicillum* species, *Streptomyces* species, mouse, etc.). Also of use are acyl CoA oxidases, classified as EC 1.3.3.6.

By the term "an intermediary enzyme" herein is meant an enzyme that generates a product that is a substrate or a cofactor for another enzyme such as another intermediary enzyme or a peroxide-generating enzyme. For instance, the soluble binding ligand may contain an enzyme, such as alkaline phosphatase (AP), that catalyzes the generation of a necessary cofactor from a phosphorylated precursor for a soluble apo-oxidase enzyme (i.e., FADP converted to FAD which binds to apo-DAAO) which in turn generates peroxide by reaction with substrate. This strategy enables cascade amplification of target binding events if the concentrations of apo-enzyme, phosphorylated cofactor, and oxidase enzyme substrate are high with respect to the surface immobilized target.

Generally, the capture binding ligand allows the attachment of a target analyte to the solid support surface, for the purposes of detection. In one embodiment, the binding is specific, and the binding ligand is part of a binding pair. By "specifically bind" herein is meant that the ligand binds the analyte, with specificity sufficient to differentiate between the analyte and other components or contaminants of the test sample. By "specific binding pair" herein is meant a complimentary pair of binding ligands such as an antibody/antigen and receptor/ligand. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-9}$ $M^{-1}$, with at least about $10^{-5}$ to $10^{-9}$ being preferred and at least about $10^{-7}$ to $10^{-9}$ $M^{-1}$ being particularly preferred.

Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Preferred binding ligand proteins include antibodies and peptides. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences.

It should also be noted that the invention described herein can also be used as a sensor for the illicit explosive triacetone triperoxide (TATP).

Anchor Groups

The present invention provides compounds including the EAM (optionally become attached to the electrode surface with a conductive oligomer), the SAM, that become bound in situ to the electrode surface. Generally, in some embodiments, these moieties are attached to the electrode using anchor group. By "anchor" or "anchor group" herein is meant a chemical group that attaches the compounds of the invention to an electrode.

As will be appreciated by those in the art, the composition of the anchor group will vary depending on the composition of the surface to which it will be attached in situ. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

Structure 1

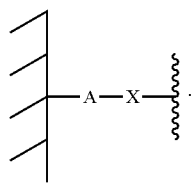

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties.

In some embodiments, the electrode is a carbon electrode, i.e. a glassy carbon electrode, and attachment is via a nitrogen of an amine group. A representative structure is depicted in Structure 15 of US Patent Application Publication No. 20080248592, hereby incorporated by reference in its entirety but particularly for Structures as described therein and the description of different anchor groups and the accompanying text. Again, additional atoms may be present, i.e. linkers and/or terminal groups.

In Structure 16 of US Patent Application Publication No. 20080248592, hereby incorporated by reference as above, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In one preferred embodiment, indium-tin-oxide (ITO) is used as the electrode, and the anchor groups are phosphonate-containing species.

Sulfur Anchor Groups

Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

Structure 2

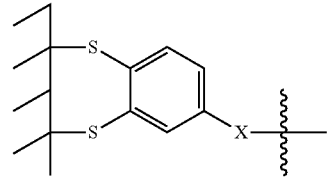

Structure 3

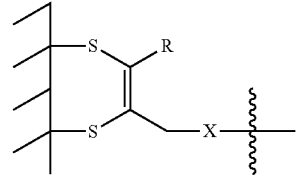

Structure 4

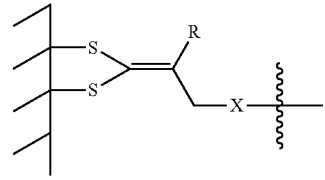

It should also be noted that similar to Structure 4, it may be possible to have a conductive oligomer terminating in a single carbon atom with three sulfur moieties attached to the electrode.

In another aspect, the present invention provides anchors comprising conjugated thiols. In some embodiments, the anchor comprises an alkylthiol group.

In another aspect, the present invention provides conjugated multipodal thio-containing compounds that serve as anchoring groups in the construction of electroactive moieties for analyte detection on electrodes, such as gold electrodes.

That is, spacer groups (which can be attached to EAMs, ReAMCs, or an "empty" monolayer forming species) are attached using two or more sulfur atoms. These mulitpodal anchor groups can be linear or cyclic, as described herein.

In some embodiments, the anchor groups are "bipodal", containing two sulfur atoms that will attach to the gold surface, and linear, although in some cases it can be possible to include systems with other multipodalities (e.g. "tripodal"). Such a multipodal anchoring group display increased stability and/or allow a greater footprint for preparing SAMs from thiol-containing anchors with sterically demanding headgroups.

In some embodiments, the anchor comprises cyclic disulfides ("bipod"). Although in some cases it can be possible to include ring system anchor groups with other multipodalities (e.g. "tripodal"). The number of the atoms of the ring can vary, for example from 5 to 10, and also includes multicyclic anchor groups, as discussed below In some embodiments, the anchor groups comprise a [1,2,5]-dithiazepane unit which is seven-membered ring with an apex nitrogen atom and a intramolecular disulfide bond as shown below:

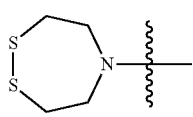

(5)

In Structure (5), it should also be noted that the carbon atoms of the ring can additionally be substituted. As will be appreciated by those in the art, other membered rings are also included. In addition, multicyclic ring structures can be used, which can include cyclic heteroalkanes such as the [1,2,5]-dithiazepane shown above substituted with other cyclic alkanes (including cyclic heteroalkanes) or aromatic ring structures. In some embodiments, the anchor group and part of the spacer has the structure shown below

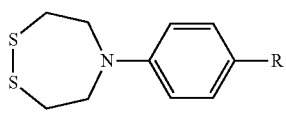

(6)

The "R" group herein can be any substitution group, including a conjugated oligophenylethynylene unit with terminal coordinating ligand for the transition metal component of the EAM.

The anchors are synthesized from a bipodal intermediate (I) (the compound as formula III where R=I), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

As will be appreciated by those in the art, the compositions of the invention can be made in a variety of ways, including those outlined below and in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; U.S. Provisional Patent Application No. 61/366,013, filed Jul. 20, 2010. In some embodiments, the composition are made according to methods disclosed in of U.S. Pat. Nos. 6,013,459, 6,248,229, 7,018,523, 7,267,939, U.S. patent application Ser. Nos. 09/096,593 and 60/980,733, and U.S. Provisional Application No. 61/087,102, filed on Aug. 7, 2008, all are herein incorporated in their entireties for all purposes.

Applications

The systems of the invention find use in the detection of a variety of target analytes, as outlined herein. In some embodiments, "sandwich" type assays are used, as are generally depicted in FIG. 6 In other embodiments, for example for the detection of particular metabolites such as cholesterol, lipids and glucose, other formats are used.

In some embodiments, for example in "sandwich" type formats, the target analyte, contained within a test sample, is added to the solid support comprising a capture binding ligand. This addition is followed by an optional washing step and the addition of the soluble binding ligand, although as will be appreciated by those in the art, these additions can be done simultaneously or the solution binding ligand can be added to the sample containing the target analyte prior to addition to the solid support. The surface is again optionally washed, and the substrate for the peroxide sensitive moiety, e.g. glucose, FAD, etc is added under conditions that if present, peroxide is generated. Peroxide containing solution is then mixed with EAM in the solution phase under conditions that the SIM is removed after the PSM reacts with peroxide. The peroxide and EAM containing solution is then delivered to the electrode. SAM formation occurs with both reacted and unreacted EAM molecules becoming bound to the electrode. The amount of reacted and unreacted EAMs can then be measure by quantifying the electrochemical signal at $E^{0}_{2}$ and $E^{0}_{1}$ respectively.

These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc. which may be used to facilitate optimal binding and/or reduce non-specific or background interactions. Also reagents that otherwise improve the efficiency of the assay, such as protease inhibitors, nuclease inhibitors, antimicrobial agents, etc., may be used. The mixture of components may be added in any order that provides for the requisite binding.

The generation of peroxide results in the loss of the PSM-SIM component of the complex, resulting in a change in the $E^0$ of the EAM. In some embodiments, the $E^0$ of the EAM changes by at about 20 mV, 30 mV, 40 mV, 50 mV, 75 mV, 80 mV, 90 mV to 100 mV, some embodiments resulting in changes of 200, 300 or 500 mV being achieved. In some embodiments, the changes in the $E^0$ of the EAM is a decrease. In some embodiments, the changes in the $E^0$ of the EAM is an increase.

Electron transfer is generally initiated electronically, with voltage being preferred. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used.

Detection

Electron transfer between the redox active molecule and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte.

The device for measuring electron transfer amperometrically involves sensitive current detection and includes a means of controlling the voltage potential, usually a potentiostat. This voltage is optimized with reference to the potential of the redox active molecule.

In some embodiments, alternative electron detection modes are utilized. For example, potentiometric (or voltammetric) measurements involve non faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capicitance) could be used to monitor electron transfer between the redox active molecules and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal to noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock in" amplifiers of detection, orders of magnitude improvements in signal to noise may be achieved.

In some embodiments, electron transfer is initiated and detected using direct current (DC) techniques. As noted above, the first $E^o$ of the redox active molecule before and the second $E^o$ of the reacted redox active molecule afterwards will allow the detection of the analyte. As will be appreciated by those in the art, a number of suitable methods may be used to detect the electron transfer.

In some embodiments, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages of from about 1 V to about +1.1 V are preferred, with from about 500 mV to about +800 mV being especially preferred, and from about 300 mV to about 500 mV being particularly preferred. On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to the first and second $E^o$ of the redox active molecules, molecules on the basis of the rate of electron transfer, which in turn can be used either to distinguish the two on the basis of frequency or overpotential.

In some embodiments, measurements of the system are taken at least two separate amplitudes or overpotentials, with measurements at a plurality of amplitudes being preferred. As noted above, changes in response as a result of changes in amplitude may form the basis of identification, calibration and quantification of the system.

In some embodiments, the AC frequency is varied. At different frequencies, different molecules respond in different ways. As will be appreciated by those in the art, increasing the frequency generally increases the output current. However, when the frequency is greater than the rate at which electrons may travel between the electrode and the redox active molecules, higher frequencies result in a loss or decrease of output signal. At some point, the frequency will be greater than the rate of electron transfer through even solvent inhibited redox active molecules, and then the output signal will also drop.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In some embodiments, measurements of the system are taken at least two separate frequencies, with measurements at a plurality of frequencies being preferred. A plurality of frequencies includes a scan. In a preferred embodiment, the frequency response is determined at least two, preferably at least about five, and more preferably at least about ten frequencies.

Signal Processing

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current will depend on a number of parameters. By varying these parameters, the system may be optimized in a number of ways.

In general, AC currents generated in the present invention range from about 1 femptoamp to about 1 milliamp, with currents from about 50 femptoamps to about 100 microamps being preferred, and from about 1 picoamp to about 1 microamp being especially preferred.

Apparatus

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands.

The apparatus further comprises a voltage source electrically connected to the test chamber; that is, to the measuring electrodes. Preferably, the voltage source is capable of delivering AC and DC voltages, if needed.

In an embodiment, the apparatus further comprises a processor capable of comparing the input signal and the output signal. The processor is coupled to the electrodes and configured to receive an output signal, and thus detect the presence of the target analyte.

EXAMPLES

Example 1

EAM solution was prepared by mixing 50 µM of EAM with 125 µM of PEG-C11-SH in ethanol. $H_2O_2$ titration was made in 100 mM $Na_2CO_3$ pH 9. 40 µL of EAM solution was added to 13 µL of each $H_2O_2$ concentration for a 30 second reaction. Final concentrations of $H_2O_2$ were 300 µM, 100 µM, and 30 µM. Then, 4 µL of Tris pH 2 was added to lower pH to 7 to stop the reaction. Final EAM/$H_2O_2$ solution was delivered to electrode for 2 minute SAM growth. Electrode was then washed 4 times with water, and 1M $LiClO_4$ was applied for cyclic voltammetry measurement.

Figure 2:
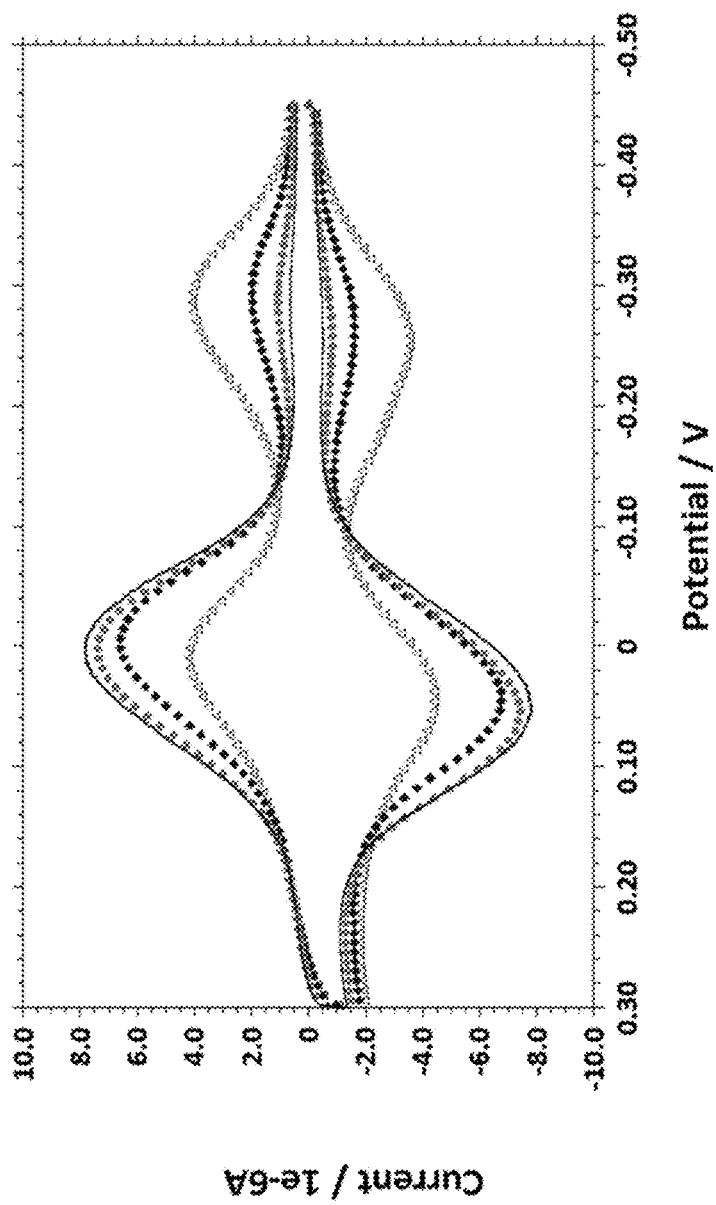
FIG. 2 illustrates feasibility data for 30-second solution based $H_2O_2$ reaction. Open triangles represent 30 μM $H_2O_2$, diamonds represent 100 μM $H_2O_2$, circles represent 300 μM $H_2O_2$, and solid line represents no $H_2O_2$.

The results of the feasibility data where the PSM in solution reacts with $H_2O_2$ homogeneously are seen in Table 1 and FIG. 2 with E-chem signal values demonstrating dose response to $H_2O_2$.

TABLE 1

Feasibility data for solution reaction with $H_2O_2$ homogeneously

| $H_2O_2$ (µM) | Average | St dev | CV |
| --- | --- | --- | --- |
| 1000 | 2.266441 | 0.582386 | 0.256961 |
| 300 | 0.905963 | 0.265597 | 0.293165 |
| 100 | 0.242688 | 0.024583 | 0.101293 |
| 30 | 0.014328 | 0.001824 | 0.12732 |
| 10 | 0.015541 | 0.006565 | 0.42241 |
| 0 | 0.004752 | 0.00159 | 0.334575 |

Data is also shown in FIG. 2 where open triangles represent 30 µM $H_2O_2$, diamonds represent 100 µM $H_2O_2$, circles represent 300 µM $H_2O_2$, and solid line represents no $H_2O_2$. Dose response demonstrated <30 µM $H_2O_2$ by measuring the current intensity of the peak at −0.25V.

Example 2

EAM solution was prepared by mixing 100 µM of EAM with 250 µM of PEG-C11-SH in ethanol. SAM growth was performed overnight, and electrodes were washed 8 times with ethanol and 4 times with water. $H_2O_2$ titration was from 300 µM, 100 µM, and 30 µM was made in $Na_2CO_3$ at pH 10. $H_2O_2$ solutions were incubated on electrodes for 30 seconds. Electrode was then washed 4 times with water, and 1M $LiClO_4$ was applied for cyclic voltammetry measurement.

Figure 3:
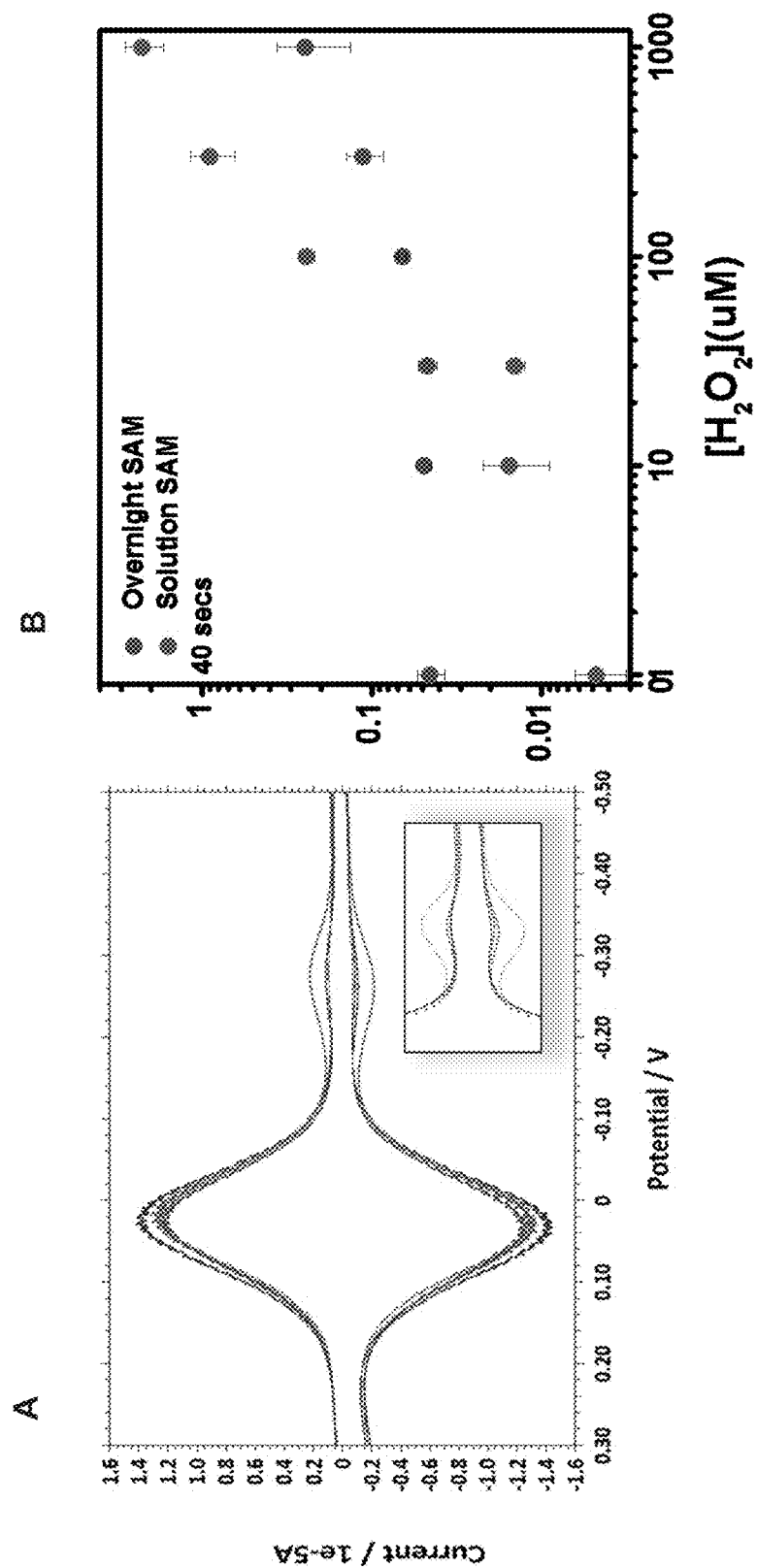
FIG. 3A shows data gathered from pre-formed SAM, surface based $H_2O_2$ reaction with 30, 100, and 300 μM $H_2O_2$.
FIG. 3B shows the dose response to $H_2O_2$ for surface and solution reactions.

Data is shown in FIG. 3A where open triangles represent 30 µM $H_2O_2$, diamonds represent 100 µM $H_2O_2$, circles represent 300 µM $H_2O_2$, and solid line represents no $H_2O_2$. Significantly less signal was observed as compared to the solution based data shown in FIG. 3B, which compares the dose response to $H_2O_2$ for surface and solution reactions.

Example 3

Surface based reaction: EAM solution was prepared by mixing 100 μM of EAM with 250 μM of PEG-C11—SH in ethanol. SAM growth was performed overnight, and electrodes were washed 8 times with ethanol and 4 times with water. $H_2O_2$ titration at 1 mM, 300 μM, 100 μM, 30 μM, 10 μM, 3 μM, and 1 μM made in 100 mM $Na_2CO_3$ at pH 10. $H_2O_2$ solutions were incubated on electrodes for 60 seconds. Electrode was then washed 4 times with water, and 1M $LiClO_4$ was applied for cyclic voltammetry measurement.

Solution based reaction: EAM solution was prepared by mixing 125 μM of EAM with 94 μM of PEG-C11-SH in ethanol. 40 μL of EAM solution was added to 60 μL of each $H_2O_2$ in 100 mM $Na_2CO_3$ at pH 10 for a 50 second reaction. Final concentrations of $H_2O_2$ were 1 mM, 300 μM, 100 μM, 30 μM, 10 μM, 3 μM, and 1 μM. Final EAM/$H_2O_2$ solution (50 μM) was delivered to electrode for 15 seconds SAM growth. Electrode was then washed 2 times with water, and 1M $LiClO_4$ was applied for cyclic voltammetry measurement.

TABLE 2

Comparison of measured E-chemistry signal for $H_2O_2$ titration

| $H_2O_2$ (μM) | AG326 Surface Reaction | AG328 Solution Reaction |
|---|---|---|
| 1000 | 0.616 | 41.166 |
| 300 | 0.260 | 1.318 |
| 100 | 0.118 | 0.319 |
| 30 | 0.043 | 0.065 |
| 10 | 0.021 | 0.017 |
| 0 | 0.004 | 0.000 |

Figure 4:
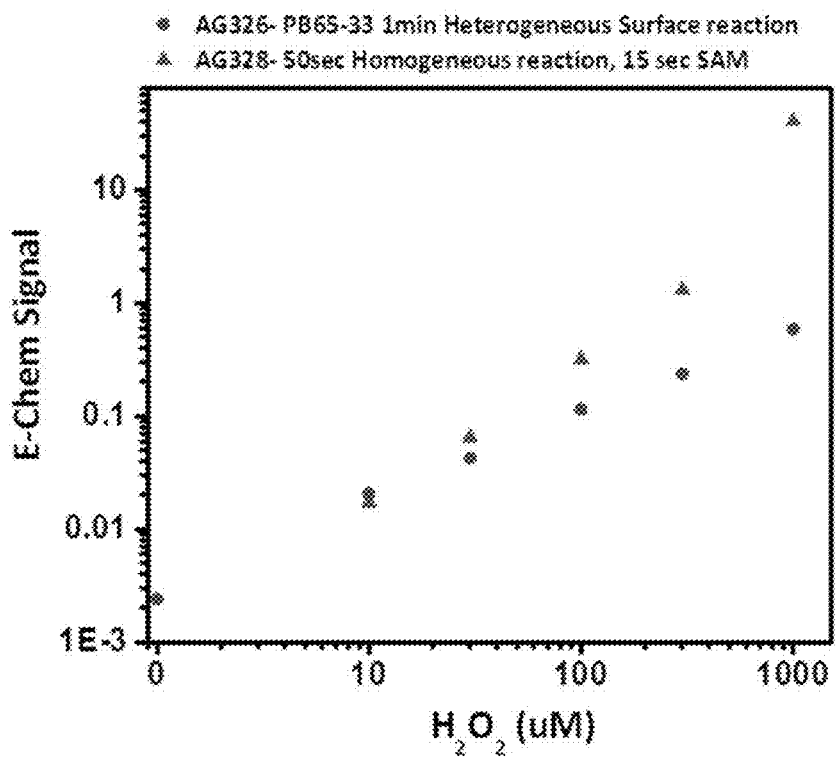
FIG. 4 shows a comparison of dose response to $H_2O_2$ for the surface and solution reaction formats at similar times (50 seconds for solution and 1 minute for surface).

Signal is significantly increased in solution reaction case. Additional data is shown in FIG. 4. Comparison of dose response to $H_2O_2$ for the surface and solution reaction formats at similar times (50 seconds for solution and 1 minute for surface). Signal significantly increased in solution reaction case and slope was higher providing larger differentiation between $H_2O_2$ concentrations which allows for enhanced sensitivity.

Example 4

Surface based reaction: EAM solution was prepared by mixing 100 μM of EAM with 250 μM of PEG-C11—SH in ethanol. SAM growth was performed overnight, and electrodes were washed 8 times with ethanol and 4 times with water. $H_2O_2$ titration at concentrations of $H_2O_2$ were at 1 mM, 300 μM, 100 μM, 30 μM, 10 μM, 3 μM, 1 μM, and 100 nM made in 100 mM $Na_2CO_3$ at pH 10. $H_2O_2$ solutions were incubated on electrodes for 10 minutes. Electrode was then washed 4 times with water, and 1M $LiClO_4$ was applied for cyclic voltammetry measurement.

Solution based reaction: EAM solution was prepared by mixing 125 μM of EAM with 94 μM of PEG-C11-SH in ethanol. 40 μL of EAM solution was added to 60 μL of each $H_2O_2$ in 100 mM $Na_2CO_3$ at pH 10 for a 90 second reaction. Final concentrations of $H_2O_2$ were 1 mM, 300 μM, 100 μM, 30 μM, 10 μM, 3 μM, and 1 μM. Final EAM/$H_2O_2$ solution (50 μM) was delivered to electrode for 90 seconds SAM growth. Electrode was then washed 2 times with water, and 1M $LiClO_4$ was applied for cyclic voltammetry measurement.

Figure 5:
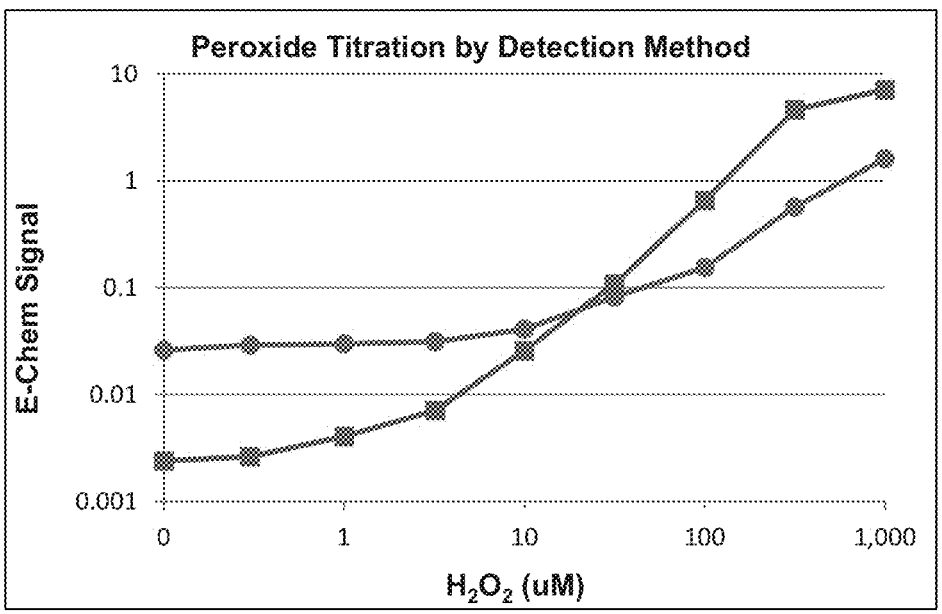
FIG. 5 a comparison of dose response to $H_2O_2$ for the surface and solution reaction formats.

Results are illustrated in FIG. 5, where the circles represent 10-minute surface based $H_2O_2$ reaction, and the squares represent 90-second solution based $H_2O_2$ reaction with 90-second SAM formation. Solution reaction produced greater signal differentiation, larger response range and higher signal for $H_2O_2$ concentrations greater than approximately 20 μM. These advantages were observed despite the surface reaction occurring for significantly longer time (10 minutes versus 3 minutes).

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

We claim:

1. A method for detecting a target analyte in a test sample, said method comprising:
   (a) contacting a test sample and a capture binding ligand that binds to a target analyte, under conditions wherein said capture binding ligand binds said target analyte, if present, in said test sample to form a first complex, said capture binding ligand bound to a first solid support;
   (b) contacting said first complex with a second binding ligand under conditions wherein said first complex and said second binding ligand bind to form a second complex, wherein said second binding ligand comprises an intermediary enzyme of a peroxide-generating system,
   (c) isolating said second complex;
   (d) contacting said second complex with a substrate for said intermediary enzyme of peroxide-generating system under conditions such that product(s) are generated to form a first assay mixture;
   (e) contacting a peroxide-generating enzyme with said first assay mixture under conditions wherein peroxide is generated to form a peroxide-containing second assay mixture;
   (f) contacting said peroxide containing second assay mixture with an electroactive moiety (EAM) comprising a transition metal complex, a self-immolative moiety (SIM), and a peroxide sensitive moiety (PSM), wherein said SIM joins the PSM to the transition metal complex and wherein said EAM has a first $E^o$, to form a third assay mixture wherein said peroxide reacts in the solution phase with said PSM of said EAM to release said SIM from said EAM and result in said EAM having a second $E^o$;
   (g) contacting said third assay mixture with a second solid support comprising an electrode under conditions such that a covalently attached self-assembled monolayer (SAM) forms comprising said EAM with said first $E^o$ and with said second $E^o$; and
   (h) detecting for a change between the first $E^o$ and the second $E^o$ of said EAM, wherein said change is an indication of the presence of said target analyte.

2. A method according to claim 1 wherein the target analyte is a protein.

3. A method according to claim 1, wherein said first solid support is chosen from the group consisting of microparticles, magnetic microparticles, beads, and microchannels.

4. A method according to claim 1, wherein said product(s) is a substrate for said peroxide-generating enzyme.

5. A method according to claim 1, further comprising the presence of a substrate for said peroxide-generating enzyme and wherein said product(s) is a cofactor for said peroxide-generating enzyme.

6. A method according to claim 1, wherein said intermediary enzyme of a peroxide-generating system is a dephosphorylating enzyme.

7. A method according to claim 6, wherein said intermediary enzyme of a peroxide-generating system is alkaline phosphatase.

8. A method according to claim 1, wherein said peroxide-generating enzyme is a flavin dependent oxidoreductase enzyme.

9. A method according to claim 8, wherein said peroxide-generating enzyme is D-amino acid oxidase.

10. A method according to claim 1, wherein said intermediary enzyme of a peroxide generating system is an oxidase enzyme.

11. A method according to claim 10, wherein said intermediary enzyme of a peroxide generating system is glucose oxidase.

12. A method according to claim 1, wherein said first binding ligand and said second binding ligand are independently chosen from the group consisting of monoclonal antibodies, fragments of monoclonal antibodies, polyclonal antibodies, fragments of polyclonal antibodies, proteins, and peptides.

13. A method according to claim 1, wherein said peroxide is hydrogen peroxide.

14. A method according to claim 1, wherein said EAM comprises a transition metal.

15. A method according to claim 14, wherein said transition metal is chosen from the group consisting of iron, ruthenium and osmium.

16. A method according to claim 1, wherein said transition metal complex is chosen from the group consisting of ferrocene and substituted ferrocene.

17. A method for detecting a target analyte in a test sample, said method comprising:
(a) contacting said target analyte with a peroxide-generating enzyme, under conditions wherein said target, if present, acts as a substrate for said peroxide-generating enzyme and peroxide is generated forming a first assay mixture;
(b) contacting said peroxide-containing first assay mixture with an electroactive moiety (EAM), said EAM comprising a transition metal complex, a self-immolative moiety (SIM), and a peroxide sensitive moiety (PSM), wherein said SIM joins the PSM to the transition metal complex and wherein said EAM has a first $E^o$ to form a second assay mixture wherein said peroxide reacts in the solution phase with said PSM of said EAM to release said SIM from said EAM and result in said EAM having a second $E^o$;
(c) contacting said second assay mixture with a first solid support comprising an electrode under conditions that a covalently attached self-assembled monolayer (SAM) forms comprising said EAM with said first $E^o$ and with said second $E^o$;
(d) detecting for a change between the first $E^o$ and the second $E^o$ of said EAM, wherein said change is an indication of the presence of said target analyte.

18. A method according to claim 17 wherein the target analyte is a small molecule.

* * * * *